United States Patent
Fulcrand et al.

(10) Patent No.: US 6,319,674 B1
(45) Date of Patent: Nov. 20, 2001

(54) METHODS FOR ATTACHING SUBSTANCES TO SURFACES

(75) Inventors: Geraldine Fulcrand; Douglas J. Dellinger, both of Sunnyvale; Steven M. Lefkowitz, Millbrae, all of CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/397,527

(22) Filed: Sep. 16, 1999

(51) Int. Cl.[7] .................................................. G01N 33/53
(52) U.S. Cl. ........................ 435/7.1; 427/341; 422/104
(58) Field of Search ................................ 435/6, 71, 7.1; 427/341; 422/104

(56) References Cited

U.S. PATENT DOCUMENTS

| | | | |
|---|---|---|---|
| 3,966,580 | 6/1976 | Janata et al. | 204/195 B |
| 4,490,216 | 12/1984 | McConnell . | |
| 4,572,901 | 2/1986 | Ceriani et al. . | |
| 4,637,861 | 1/1987 | Krull et al. . | |
| 4,661,235 | 4/1987 | Krull et al. | 204/414 |
| 4,680,121 | 7/1987 | Ramsden et al. . | |
| 4,812,512 | 3/1989 | Buendia et al. | 525/54.11 |
| 4,927,879 | 5/1990 | Pidgeon | 525/54.1 |
| 4,931,498 | 6/1990 | Pidgeon | 525/54.1 |
| 4,948,882 | 8/1990 | Ruth | 536/27 |
| 5,002,884 | 3/1991 | Kobayashi et al. . | |
| 5,043,278 | 8/1991 | Nagaoka et al. . | |
| 5,063,109 | 11/1991 | Bieniarz, et al. | 428/378 |
| 5,112,962 | 5/1992 | Letsinger et al. | 536/27 |
| 5,143,854 | 9/1992 | Pirrung et al. | 436/518 |
| 5,187,066 | 2/1993 | Becker et al. | 435/7.36 |
| 5,204,239 | 4/1993 | Gitler et al. | 435/7.1 |
| 5,258,041 | 11/1993 | Guire et al. . | |
| 5,314,830 | 5/1994 | Anderson et al. . | |
| 5,372,930 | 12/1994 | Colton et al. | 435/6 |
| 5,393,877 | 2/1995 | McLean et al. | 536/25.3 |
| 5,405,766 | 4/1995 | Kallury et al. | 435/174 |
| 5,405,783 | 4/1995 | Pirrung et al. | 436/518 |
| 5,436,327 | 7/1995 | Southern et al. | 536/25.34 |
| 5,445,934 | 8/1995 | Fodor et al. | 435/6 |
| 5,491,097 | 2/1996 | Ribi et al. | 436/518 |
| 5,516,703 | 5/1996 | Caldwell et al. | 436/532 |
| 5,552,535 | 9/1996 | McLean et al. | 536/23.1 |
| 5,571,568 | 11/1996 | Ribi et al. | 427/487 |
| 5,585,236 | 12/1996 | Bonn et al. . | |
| 5,601,979 | 2/1997 | Wong . | |
| 5,610,274 | 3/1997 | Wong . | |
| 5,614,263 | 3/1997 | Ogawa et al. . | |
| 5,622,872 | 4/1997 | Ribi | 436/518 |
| 5,624,711 | 4/1997 | Sundberg et al. . | |
| 5,637,201 | 6/1997 | Raguse et al. . | |
| 5,656,744 | 8/1997 | Arnold, Jr. et al. | 536/25.3 |
| 5,679,539 | 10/1997 | Hudson et al. | 435/68.1 |
| 5,728,588 | 3/1998 | Caldwell et al. | 436/532 |
| 5,734,020 | 3/1998 | Wong | 530/350 |
| 5,744,101 | 4/1998 | Foder et al. | 422/131 |
| 5,846,724 | * 12/1998 | Bensimon et al. | 435/6 |

OTHER PUBLICATIONS

U.S. Patent Application entitled "Functionalization of Substrate Surfaces with Silane Mixtures,"U.S. Ser. No. 09/145, 015, filed Sep. 1, 1998. (Steven M. Lefkowitz, Geraldine Fulcrand, Douglas J. Dellinger and Charles Z. Hotz).

* cited by examiner

*Primary Examiner*—Scott W. Houtteman

(57) ABSTRACT

Methods are disclosed for immobilizing a substance to a surface. A surface is employed that comprises a linking group consisting of a first portion comprising a hydrocarbon chain, optionally substituted, and a second portion comprising an alkylene oxide or an alkylene imine wherein the alkylene is optionally substituted. One end of the first portion is attached to the surface and one end of the second portion is attached to the other end of the first portion chain by means of an amine or an oxy functionality. The second portion terminates in an amine or a hydroxy functionality. The surface is reacted with the substance to be immobilized under conditions for attachment of the substance to the surface by means of the linking group. Compositions of matter and reaction systems are also disclosed.

28 Claims, 12 Drawing Sheets

Linker #1 (ALTA) X=NHCH$_2$ ; Y=CH$_2$NH$_2$
Linker #2 X=NHCH$_2$ ; Y=CH$_2$OH
Linker #3 (ALTO) X=O; Y=OH Figure 1: Modular Linker Surfaces Figure 2: In Situ Oligonucleotide Synthesis on ALTA Surface (Cleavable Linker)

Figure 3: In Situ Oligonucleotide on ALTO Surface

Figure 4: ALTA and ALTO Surfaces

Figure 5: Conversion of ALTA and ALTO Surfaces to Amine-Reactive Surfaces

Figure 6: Hybridization Signal

Figure 7: Hybridization Signal

Figure 9: Comparison of Batch to Batch Amine Density Variation aScheme III: Synthesis of Bifunctional Linker 10 a(i) 4-AnisylMgBr/THF/16 h; (ii) 3-BrPropyl phthalimide/toluene/Δ/24 h; (iii) H₂NNH₂.xH₂O/EtOH/Δ/1 h; (iv) bis-4-Nitrophenyl carbonate/DCM/16 h; (v) AcCl/Hexanes/Δ/6 h; (vi) 2'-Deoxythymidine/pyridine/2 h; (vii) 4-Chlorophenyl chloroformate/pyridine/1 h.

METHODS FOR ATTACHING SUBSTANCES TO SURFACES

BACKGROUND OF THE INVENTION

1. Field of the Invention

This invention relates to the covalent attachment of a substance such as a biological moiety to a surface such as, for example, a glass surface, metal or metal oxide. One area of use of the present invention is in the field of solid phase chemical synthesis, particularly solid phase synthesis of oligomer arrays, or attachment of oligonucleotides and polynucleotides to surfaces, e.g., arrays of polynucleotides.

In the field of diagnostics and therapeutics, it is often useful to attach species to a surface. One important application is in solid phase chemical synthesis wherein initial derivatization of a substrate surface enables synthesis of polymers such as oligonucleotides and peptides on the substrate itself. Intact oligonucleotides, polynucleotides, peptides or proteins may be attached to a surface or a substrate in a similar manner. Support bound oligomer arrays, particularly oligonucleotide arrays, may be used in screening studies for determination of binding affinity. Modification of surfaces for use in chemical synthesis has been described. See, for example, U.S. Pat. No. 5,624,711 (Sundberg), U.S. Pat. No. 5,266,222 (Willis) and U.S. Pat. No. 40 5,137,765 (Farnsworth).

In modifying siliceous or metal oxide surfaces, one technique that has been used is derivatization with bifunctional silanes, i.e., silanes having a first functional group enabling covalent binding to the surface (often an Si-halogen or Si-alkoxy group, as in $-SiCl_3$ or $-Si(OCH_3)_3$, respectively) and a second functional group that can impart the desired chemical and/or physical modifications to the surface. A problem with this type of surface modification, however, is that incorporation of a desirable surface chemical functionality provided by the second functional group requires chemical compatibility between the two functional groups. The presence of the second functional group can affect the density, uniformity and reproducibility of the surface coverage.

There are a number of applications for polynucleotides bound to solid supports. For example, such supports may be used to test for the presence of mutations in complex DNA's, e.g., for disease loci in humans. They can be used also to select specific nucleic acids form complex mixtures, for example, specific mRNA's from a whole cell population.

In the field of bioscience, arrays of oligonucleotide probes, fabricated or deposited on a surface, are used to identify DNA sequences in cell matter. The arrays may be used for conducting cell study, for diagnosing disease, identifying gene expression, monitoring drug response, determination of viral load, identifying genetic polymorphisms, and the like. Significant morbidity and mortality are associated with infectious diseases and genetically inherited disorders. More rapid and accurate diagnostic methods are required for better monitoring and treatment of these conditions. Molecular methods using DNA probes, nucleic acid hybridization and in vitro amplification techniques are promising methods offering advantages to conventional methods used for patient diagnoses.

Proteins have been immobilized in the past on a wide variety of solid supports for various known applications including analysis, separation, synthesis and detection of biological and other materials. Often hydrophilic polymers have been used to immobilize the proteins because it is less difficult to attach proteins to polymers than to inorganic materials. However, there is an increasing need to immobilize functional organic material such as proteins on inorganic material such as silica, glass, silicon, metals and the like. In solid phase technology the reagent or reagents used in the procedure are usually immobilized by being coated or bonded either covalently or by adsorption to the solid phase material.

Biologically active polypeptides or proteins that are attached to insoluble carrier material, such as polymeric particles, have been used in a variety of ways. For example, the diagnosis of pathological or other conditions in human beings and animals is often carried out using immunological principles for the detection of an immunologically reactive species, for example, antibodies or an antigen, in the body fluids of the person or animal. Other proteins and amine-containing compounds, such as enzymes, avidin, biotin or polysaccharides, have been covalently linked to various carrier materials for use in affinity chromatography, enzymatic reactions, specific binding reactions and immunoassays.

A variety of methods have been reported for the covalent attachment of ligands to a surface. Typically, these reactions are performed by the reaction of an active functional group on the ligand with an activated functional group on the surface. Other reactions, such are UV cross-linking, can be used for covalent attachment but are not functional group type-specific. Functional group specific methods previously described include the activation of surfaces with cyanogen bromide, N-hydroxysuccinimide esters, carbonyl diimidazole, carbodiimides, azlactones, cyanuric chlorides, organic sulfonyl chlorides, divinyl sulphone, nitrophenyl esters, iodoacetyl, maleimide, epoxy, hydrazide, reductive amination, diazonium salts and Mannich condensations. Ligands that react with the activated surface include amines, alcohols, carboxylic acids, thiols, carbonyls, and compounds containing active hydrogens. Other approaches involve treating the surface of an inorganic support with N-(2-aminoethyl)-3-aminopropyltrimethoxysilane or 3-aminopropyltriethoxysilane with the amino group as an attachment point.

Many of the known procedures for attaching monomers, oligomers and polymers to surfaces to form arrays exhibit a significant amount of batch to batch variability. This is often not acceptable because there is a significant impact on the accuracy and reproducibility of quantitative determinations. For such determinations it is important to be able to prepare arrays that show consistency in the performance of the array particularly from one batch to the next.

The present invention is directed to the aforementioned need in the art and provides a way of obtaining a high density, reproducible and uniform coverage of a surface while avoiding the aforementioned problems and difficulties associated with the procedures in the art.

2. Description of the Related Art

U.S. Pat. No. 5,258,041 (Guire, et al.) discloses a method of biomolecule attachment to hydrophobic surfaces.

U.S. Pat. No. 5,043,278 (Nagaoka, et al.) discusses physiologically active substance fixed to a thin fiber carrier with an alkylene oxide chain.

U.S. Pat. No. 5,314,830 (Anderson, et al.) discloses immobilized hydrophobically modified antibodies.

U.S. Pat. No. 5,624,711 (Sundberg, et al.) discusses derivatization of solid supports and methods for oligomer synthesis.

U.S. Pat. No. , 4,680,121 (Ramsden, et al.) discloses bonded phase of silica for solid phase extraction.

U.S. Pat. No. 5,002,884 (Kobayashi, et al.) discusses immobilization of physiologically active substances on an inorganic support.

U.S. Pat. No. 5,436,327 (Southern, et al.) discloses support bound oligonucleotides.

U.S. Pat. No. 5,585,236 (Bonn, et al.) discusses nucleic acid separation on alkylated nonporous polymer beads.

U.S. Pat. No. 5,601,979 (Wong 1) discloses preparation and use of magnetic controlled pore glass having oligonucleotides synthesized thereon.

U.S. Pat. No. 5,637,201 (Raguse, et al.) discusses sensor membranes.

U.S. Pat. No. 5,614,263 (Ogawa, et al.) discusses hydrophilic chemically adsorbed film and method of manufacturing the same.

U.S. Pat. No. 5,610,274 (Wong 2) discloses preparation and use of magnetic porous inorganic materials.

U.S. Pat. No. 4,490,216 (McConnell) discusses lipid membrane electroanalytical elements and method of analysis therewith.

U.S. Pat. No. 4,572,901 (Ceriani, et al.) discusses a method and composition for protein immobilization.

U.S. Pat. No. 4,637,861 (Knill, et al) discusses stabilized lipid membrane based device and method of analysis.

U.S. Pat. No. 9839481 (Anderson, et al.) discloses attachment of nucleic acids to solid phase surfaces via disulphide bonds.

SUMMARY OF THE INVENTION

One aspect of the present invention is a method for immobilizing a substance to a surface. A surface is employed that comprises a linking group consisting of a first portion comprising a hydrocarbon chain, optionally substituted, and a second portion comprising an alkylene oxide or an alkylene imine wherein the alkylene is optionally substituted. One end of the first portion is attached to the surface and one end of the second portion is attached to the other end of the first portion chain by means of an amine or an oxy functionality. The second portion terminates in an amine or a hydroxy functionality. The surface is reacted with the substance to be immobilized under conditions for attachment of the substance to the surface by means of the linking group.

Another aspect of the present invention is a composition of the formula:

$$Z\text{-}\{SiR^1R^2\text{---}CH_2(CH_2)_tCH_2\text{---}Y\text{---}(CH_2)_{m'}\text{---}[O\text{---}(CH_2)_{n'}]_u\text{---}O\text{---}(CH_2)_{p'}\text{---}X\}_V$$

wherein:
Z is a surface,
$R^1$ and $R^2$ are independently O, alkyl, aryl, alkoxy, aryloxy or halogen,
t is an integer of about 2 to about 24,
m', n' and p' are each independently integers of about 1 to about 4,
u is an integer of about 1 to about 24,
v represents a surface density of about 1 to about $1 \times 10^7$ molecules per square micron,
Y is O or $NR^3$ wherein $R^3$ is H or alkyl, and
X is OH, $NR^4R^5$ wherein $R^4$ and $R^5$ are each independently H or alkyl or L-D wherein L is a linking group or a bond and D is a ligand or a receptor.

Another aspect of the present invention is a reaction system comprising:

(a) a composition of the formula:

$$Z\text{-}\{SiR^1R^2\text{---}CH_2(CH_2)_tCH_2\text{---}A\}_{v'}$$

wherein:
Z is a surface,
$R^1$ and $R^2$ are independently O, alkyl, aryl, alkoxy, aryloxy, or halogen,
v represents a surface density of about 1 to about $1 \times 10^7$ molecules per square micron,
t is an integer of about 2 to about 24, and
A is a leaving group, and (b) a composition of the formula:

$$W\text{---}(CH_2)_{m'}\text{---}[O\text{---}(CH_2)_{n'}]_u\text{---}(CH_2)_{p'}\text{---}X$$

wherein:
m', n' and p' are each independently integers of about 1 to about 4,
u is an integer of about 1 to about 24,
W is OH or $NHR^6$ wherein $R^6$ is H or alkyl, and
X is OH, $NR^4R^5$ wherein $R^4$ and $R^5$ are each independently H or alkyl or L'—D'
wherein L' is a linking group or a bond and D' is a ligand or a receptor.

Another aspect of the present invention is a method for immobilizing a substance to a surface. The method comprises:

(a) combining in a reaction medium
(i) the substance,
(ii) a first composition of the formula:

$$Z\text{-}\{SiR^1R^2\text{---}CH_2(CH_2)_tCH_2\text{---}A\}_{v'}$$

wherein:
Z is a surface,
$R^1$ and $R^2$ are independently O, alkyl, aryl, alkoxy, aryloxy, or halogen,
t is an integer of about 2 to about 24, and
A is a leaving group, and (iii) a second composition of the formula:

$$W\text{---}(CH_2)_{m'}\text{---}[O\text{---}(CH_2)_{n'}]_u\text{---}(CH_2)_{p'}\text{---}X$$

wherein:
m', n' and p' are each independently integers of about 1 to about 4,
u is an integer of about 1 to about 24,
v represents describes a surface density of about 1 to about $1 \times 10^7$ molecules per square micron,
W is OH or $NHR^6$ wherein $R^6$ is H or alkyl, and
X is OH, $NR^4R^5$ wherein $R^4$ and $R^5$ are each independently H or alkyl or —L—D' wherein L is a linking group or a bond and D' is an amine or a hydroxyl group and (b) treating the medium under conditions sufficient to permit the second composition to attach to the first composition and the substance to attach to the second composition.

DEFINITIONS

Figure 1:
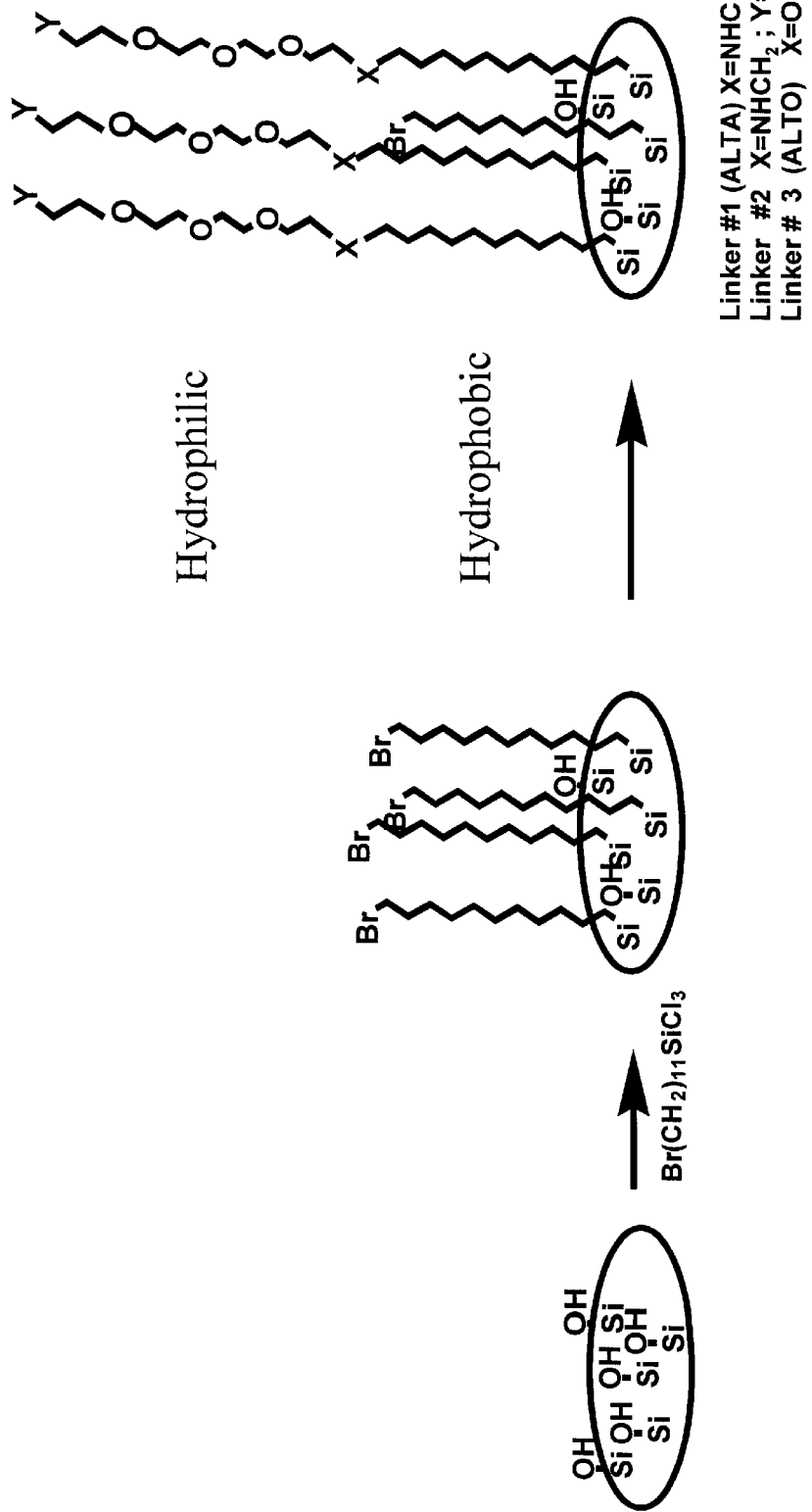
FIG. 1 is a schematic diagram depicting one aspect of the present invention.

Before proceeding further with a description of the specific embodiments of the present invention, a number of terms will be defined.

Substance—the moiety to be immobilized. In general, the substance may be a ligand or a receptor.

Ligand—any moiety for which a receptor naturally exists or can be prepared. The ligand may be an organic compound, which may be either a small molecule or a large molecule or macromolecule. The ligand may be a protein, peptide, polysaccharide, hormone, nucleic acid, liposome, cell, label, hapten, drug, inhibitor and so forth.

For the most part, the large molecule ligands to which the subject invention can be applied include poly(aminoacid), e.g., proteins, large peptides, polysaccharides, hormones, nucleic acids, e.g., oligonucleotides, polynucleotides and so forth. The large molecules generally have a molecular weight of at least about 5,000, more usually at least about 10,000. In the poly(amino acid), polysaccharide or nucleic acid category, the molecules are generally from about 5,000 to about 5,000,000 molecular weight, more usually from about 20,000 to about 1,000,000 molecular weight. In the hormone category, the molecular weights usually range from about 5,000 to about 60,000.

A wide variety of proteins are included within the term "large molecules." Such proteins include proteins having particular biological functions, proteins related to specific microorganisms, particularly disease causing microorganisms, etc. Exemplary of such proteins are immunoglobulins, cytokines, enzymes, hormones, cancer antigens, nutritional markers, tissue specific antigens, etc. Such proteins include, by way of illustration and not limitation, protamines, histones, albumins, globulins, scleroproteins, phosphoproteins, mucoproteins, chromoproteins, lipoproteins, nucleoproteins, glycoproteins, T-cell receptors, proteoglycans, HLA, unclassified proteins, e.g., somatotropin, prolactin, insulin, pepsin, proteins found in human plasma, blood clotting factors, protein hormones such as, e.g., follicle-stimulating hormone, luteinizing hormone, luteotropin, prolactin, chorionic gonadotropin, tissue hormones, cytokines, cancer antigens such as, e.g., PSA, CEA, a-fetoprotein, acid phosphatase, CA19.9 and CA125, tissue specific antigens, such as, e.g., alkaline phosphatase, myoglobin, CPK-MB and calcitonin, and peptide hormones.

Polynucleotides include single-stranded or double-stranded DNA, RNA, modified DNA, modified RNA, m-RNA, r-RNA, t-RNA, cDNA, DNA-RNA duplexes, etc.

The small molecules are generally of molecular weight less than about 5,000, more usually less than about 2000 and include haptens, which are molecules that are not immunogenic by themselves but can be rendered immunogenic by being attached to a large molecule. Usually, the lower molecular weight or small molecules are generally of from about 100 to about 2,000 molecular weight, more usually from about 125 to about 1,000 molecular weight. The small molecules include drugs, metabolites, pesticides, pollutants, lower molecular weight peptides, oligonucleotides, nucleotides and nucleosides and so forth.

The term "drug" includes alkaloids, steroids, barbituates, amphetamines; catecholamines, benzheterocyclics, the heterocyclic rings being azepines, diazepines and phenothiazines, purines, which includes theophylline, caffeine, drugs derived from marijuana, hormones, vitamins, prostaglandins, tricyclic antidepressants, anti-neoplastics, antibiotics, nucleosides and nucleotides, miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives, aminoglycosides, opiods and the like.

Metabolites related to diseased states include spermine, galactose, phenylpyruvic acid, and porphyrin Type 1. Among pesticides are polyhalogenated biphenyls, phosphate esters, thiophosphates, carbamates, polyhalogenated sulfenamides, their metabolites and derivatives.

Receptor—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component Clq, and the like. The term "receptor" also includes polynucleotide binding agents, such as, for example, restriction enzymes, activators, repressors, nucleases, polymerases, histones, repair enzymes, chemotherapeutic agents, and the like. For receptors, the molecular weights will generally range from about 10,000 to about 2×10$^8$, more usually from about 10,000 to about 10$^6$. For immunoglobulins, IgA, IgG, IgE and IgM, the molecular weights will generally vary from about 160,000 to about 10$^6$. Enzymes will normally range from about 10,000 to about 1,000,000 in molecular weight. Natural receptors vary widely, generally being at least about 25,000 molecular weight and may be about 10$^6$ or higher molecular weight, including such materials as avidin, DNA, RNA, thyroxine binding globulin, thyroxine binding prealbumin, transcortin, etc. As can be seen there is some overlap between large molecular ligands on the one hand and receptors on the other hand.

Linking group—a group for attaching one moiety to another moiety, usually by covalent linkage.

Hydrocarbon chain—a chain of carbon atoms, usually about 5 to about 40 carbon atoms, more usually, about 6 to about 20 carbon atoms. The chain may comprise an alkyl chain, an alkenyl chain, cycloalkyl group, aryl group, and the like or a combination of straight and branched chain and/or cyclic groups.

"Alkyl" means a branched or unbranched saturated monovalent hydrocarbon radical containing 1 to about 30 or more carbon atoms, such as methyl, ethyl, propyl, tert-butyl, n-hexyl, n-octyl and the like.

"Lower alkyl" means a branched or unbranched saturated monovalent hydrocarbon radical containing 1 to about 10 carbon atoms, such as methyl, ethyl, propyl, isopropyl, tert-butyl, butyl, n-pentyl and the like, unless otherwise indicated.

"Cycloalkyl" means a saturated monovalent monocyclic hydrocarbon radical containing about 3 to about 8 carbon atoms, such as cyclopropyl, cyclobutyl, cyclopentyl, cyclohexyl, cycloheptyl and cyclooctyl.

"Alkylene" means a branched or unbranched saturated divalent hydrocarbon radical containing 1 to 30 carbon atoms, such as methylene, ethylene, propylene, 2-methylpropylene, 1,2-dimethylpropylene, pentylene, and the like.

"Lower alkenyl" means a branched or unbranched unsaturated hydrocarbon radical containing at least one ethenylic bond (carbon-carbon double bond) and 2 to 10 carbon atoms.

"Alkenylene" means a branched or unbranched unsaturated divalent hydrocarbon radical containing at least one ethenylic bond and about 2 to about 30 carbon atoms, such as ethenylene, propenylene, 2-methylpropenylene, 1,2-dimethylpropenylene, pentenylene, and the like.

"Lower alkenylene" means a branched or unbranched unsaturated divalent hydrocarbon radical containing at least one ethenylic bond and about 2 to about 10 carbon atoms.

Alkoxy means a substituent —O—R wherein R is alkyl as defined above. The term "lower alkoxy" refers to such a group wherein R is lower alkyl.

Alkylene oxide—a chain comprising repeating units of alkylene and oxygen in an ether linkage, usually comprising from about 2 to about 100, more usually from about 4 to about 50, alkylene units and from about 2 to about 60, more usually, about 4 to about 30, oxygen atoms. For example, the alkylene oxide may be represented by the formula: O—$(CH_2)_m$—[O—$(CH_2)_n]_q$—O—$(CH_2)_p$—O wherein m, n and p, are each independently an integer of 1 to about 4, preferably, m=n=p=2 and q is an integer of 1 to about 24, preferably 1 to about 10, more preferably 1 to about 4, desirably 2. The alkylene moiety may be optionally substituted with one or more alkyl groups, cycloalkyl groups, aryl groups, heterocyclic groups, and the like and combinations thereof.

Alkylene imine—a chain comprising repeating units of akylene and nitrogen as an imine linkage, usually comprising from about 2 to about 100, more usually from about 4 to about 50, alkylene units and from about 2 to about 60, more usually, about 4 to about 30, nitrogen atoms. For example, the akylene imine may be represented by the formula: N—$(CH_2)_m$—[NR—$(CH_2)_{n-1}]_q$—NR—$(CH_2)_p$—N wherein R is H or alkyl, m, n, and are each independently an integer of 1 to about 4, preferably, m=n=p=2 and q is an integer of 1 to about 24, preferably 1 to about 10, more preferably 1 to 4, even more preferably 2. The alkylene moiety may be optionally substituted with one or more alkyl groups, cycloalkyl groups, aryl groups, heterocyclic groups, and the like and combinations thereof.

Optionally substituted—means that a hydrogen atom of a molecule may be replaced by another atom, which may be a single atom such as a halogen, or heteroatom, or part of a group of atoms forming, for example, alkyl groups, heteroatom substituted alkyl groups, cyclic structures or heterocyclic structures.

Halogen or halo—means chlorine or chloro, bromine or bromo, iodine or iodo or fluorine or fluoro.

Silyl linkage—a linkage that involves a silicon atom. Usually, a silicon oxygen bond, a silicon halogen bond, a silicon nitrogen bond, or a silicon carbon bond.

Functionalization—relates to modification of a solid substrate to provide a plurality of functional groups on the substrate surface. By the term "functionalized surface" is meant a substrate surface that has been modified so that a plurality of functional groups are present thereon.

Reactive hydrophilic site or reactive hydrophilic group—refers to hydrophilic moieties that can be used as the starting point in a synthetic organic process. This is in contrast to "inert" hydrophilic groups that could also be present on a substrate surface, e.g., hydrophilic sites, associated with polyethylene glycol, a polyamide or the like.

Monomer—a chemical entity that can be covalently linked to one or more other such entities to form an oligomer or polymer. Examples of monomers include nucleotides, amino acids, saccharides, peptoids, and the like. In general, the monomers used in conjunction with the present invention have first and second sites (e.g., C-termini and N-termini, or 5' and 3' sites) suitable for binding of other like monomers by means of standard chemical reactions (e.g., condensation, nucleophilic displacement of a leaving group, or the like), and a diverse element that distinguishes a particular monomer from a different monomer of the same type (e.g., an amino acid side chain, a nucleotide base, etc.). The initial substrate-bound monomer is generally used as a building block in a multi-step synthesis procedure to form a complete ligand, such as in the synthesis of oligonucleotides, oligopeptides and the like.

Oligomer—a chemical entity that contains a plurality of monomers. As used herein the terms "oligomer" and "polymer" are used interchangeably as it is generally although not necessarily smaller "polymers" that are prepared or attached using the functionalized substrates of the present invention. Example oligomers and polymers include polydeoxyribonucleotides, polyribonucleotides, other polynucleotides that are C-glycosides of a purine or pyrimidine base, or other modified polynucleotides, polypeptides, polysaccharides, and other chemical entities that contain repeating units of like chemical structure. In the practice of the present invention, oligomers generally comprise about 6 to about 20,000 monomers, preferably, about 10 to about 10,000, more preferably about 15 to about 4,000 monomers.

Amino acid—includes not only the L-, D- and non-chiral forms of naturally occurring amino acids (alanine, arginine, etc.) but also modified amino acids, amino acid analogs, and other chemical compounds that can be incorporated in conventional oligopeptide synthesis, e.g., 4-nitrophenylalanine, isoglutamic acid, isoglutamine, ε-nicotinoyllysine, isonipecotic acid, tetrahydroisoquinoleic acid, α-aminoisobutyric acid, sarcosine, citrulline, cysteic acid, t-butylglycine, t-butyl alanine, phenylglycine, cyclohexylalanine, β-alanine, 4aminobutyric acid and the like.

Protection and deprotection—relate to the addition and removal of chemical protecting groups using conventional materials and techniques within the skill of the art and/or described in the pertinent literature; for example, reference can be made to Greene, et al., Protective Groups in Organic Synthesis, $2^{nd}$ Ed., New York, John Wiley & Sons (1991). Protecting groups prevent the site to which they are attached from participating in the chemical reaction to be carried out.

Leaving group—a group that is subject to displacement by another group in a reaction such as an $S_N1$ or $S_N2$ reaction. In general, there is a reasonable correlation between the ability of a group to be displaced and the acid strength of the group when bound to hydrogen. The stronger the acid that comprises the group, the better the leaving capability of the leaving group.

Amine reactive functional group—a functional group that reacts with an amine group, preferably, one that reacts specifically with an amine group. Such groups include by way of illustration and not limitation isocyanate, thioisocyanate, N-hydroxysuccinimidyl, p-nitrophenyl ester or pentafluorophenyl ester, carbonyl imidazole, carbonates, aldehydes, and so forth.

Alcohol reactive functional group—a functional group that reacts with an alcohol group, preferably, a group that reacts specifically with an alcohol group. Such groups include by way of illustration and not limitation phosphoramidites, triphenylphosphine, H-phosphonate diesters, esters, sulfonic acid esters, anhydrides, acyl halides, halogens, silyl ethers, trityl halides and so forth.

Surface—the outer portion of a support, which is a porous or non-porous water insoluble material. The support can have any one of a number of shapes, such as strip, plate, disk, rod, particle, including bead, tube, well, and the like. The support can be hydrophilic or capable of being rendered hydrophilic and includes inorganic powders such as glass, silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly (vinyl butyrate), etc.; either used by themselves or in conjunction with other materials; glass available as Bioglass, ceramics, metals and metal oxides, and the like. Natural or synthetic assemblies such as liposomes, phospholipid vesicles, and cells are also included within the meaning of the term "support."

Label—a member of a signal producing system. The label is capable of being detected directly or indirectly. In general, any reporter molecule that is detectable can be a label. Labels include (i) reporter molecules that can be detected directly by virtue of generating a signal, (ii) specific binding pair members that may be detected indirectly by subsequent binding to a cognate that contains a reporter molecule, (iii) oligonucleotide primers that can provide a template for amplification or ligation or (iv) a specific polynucleotide sequence or recognition sequence that can act as a ligand such as for a repressor protein, wherein in the latter two instances the oligonucleotide primer or repressor protein will have, or be capable of having, a reporter molecule covalently attached, and so forth.

The reporter molecule can be isotopic or nonisotopic, usually nonisotopic, and can be a catalyst, such as an enzyme, a polynucleotide coding for a catalyst, promoter, dye, fluorescent molecule, chemiluminescent molecule, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, and the like. The reporter molecule can be a fluorescent group such as fluorescein, a chemiluminescent group such as luminol, a terbium chelator such as N-(hydroxyethyl) ethylenediaminetriacetic acid that is capable of detection by delayed fluorescence, and the like. The label is often a part of a signal producing system, which includes all of the reagents required to produce a measurable signal. Components of the signal producing system other than the label may be included in a developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like.

Member of a specific binding pair ("sbp member")—one of two different molecules, having an area on the surface or in a cavity which specifically binds to and is thereby defined as complementary with a particular spatial and polar organization of the other molecule. The members of the specific binding pair include ligand and receptor (antiligand). These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like are not immunological pairs but are included in the invention and the definition of sbp member.

Antibody—an immunoglobulin that specifically binds to and is thereby defined as complementary with a particular spatial and polar organization of another molecule. The antibody can be found in the blood of an animal or may be synthesized. Monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and $F(ab')_2$, Fab', and the like. In addition, aggregates, polymers, and conjugates of immunoglobulins or their fragments can be used where appropriate so long as binding affinity for a particular molecule is maintained.

Polynucleotide—a compound or composition that is a polymeric nucleotide or nucleic acid polymer. The polynucleotide may be a natural compound or a synthetic compound, single stranded or double stranded. In the context of an assay, the polynucleotide is often referred to as a polynucleotide analyte. The polynucleotide can have from about 2 to 5,000,000 or more nucleotides. The larger polynucleotides are generally found in the natural state. In an isolated state the polynucleotide can have about 2 to 50,000 or more nucleotides, usually about 10 to 20,000 nucleotides, more frequently 100 to 10,000 nucleotides. It is thus obvious that isolation of a polynucleotide from the natural state often results in fragmentation. The polynucleotides include nucleic acids, and fragments thereof, from any source in purified or unpurified form including DNA (dsDNA and ssDNA) and RNA, including tRNA, mRNA, rRNA, mitochondrial DNA and RNA, chloroplast DNA and RNA, DNA/RNA hybrids, or mixtures thereof, genes, chromosomes, plasmids, the genomes of biological material such as microorganisms, e.g., bacteria, yeasts, viruses, viroids, molds, fungi, plants, animals, humans, and the like.

The polynucleotide can be only a minor fraction of a complex mixture such as a biological sample. Also included are genes, such as hemoglobin gene for sickle-cell anemia, cystic fibrosis gene, oncogenes, cDNA, and the like.

Oligonucleotide—a polynucleotide, usually single stranded, usually a synthetic polynucleotide but may be a naturally occurring polynucleotide. The oligonucleotide(s) are usually comprised of a sequence of at least about 5 nucleotides, preferably, about 10 to about 100 nucleotides, more preferably, about 20 to about 50 nucleotides, and usually about 10 to about 30 nucleotides, more preferably, about 15 to about 30 nucleotides.

Methods of oligonucleotide synthesis include phosphotriester and phosphodiester methods (Narang, et al. (1979) Meth. Enzymol 68:90) and synthesis on a support (Beaucage, et al. (1981) Tetrahedron Letters 22:1859–1862) as well as phosphoramidite techniques (Caruthers, M. H., et al., "Methods in Enzymology," Vol. 154, pp. 287–314 (1988)) and others described in "Synthesis and Applications of DNA and RNA," S. A. Narang, editor, Academic Press, New York, 1987, and the references contained therein.

Oligonucleotide probe—an oligonucleotide employed to bind to a portion of a polynucleotide such as another oligonucleotide or a target nucleotide sequence. The design and preparation of the oligonucleotide probes are generally dependent upon the sensitivity and specificity required, the sequence of the target polynucleotide and, in certain cases, the biological significance of certain portions of the target polynucleotide sequence.

Nucleoside triphosphates—nucleosides having a 5'-triphosphate substituent. The nucleosides are pentose sugar derivatives of nitrogenous bases of either purine or pyrimidine derivation, covalently bonded to the 1'-carbon of the pentose sugar, which is usually a deoxyribose or a ribose. The purine bases include adenine (A), guanine (G), inosine (I), and derivatives and analogs thereof. The pyrimidine bases include cytosine (C), thymine (T), uracil (U), and derivatives and analogs thereof. Nucleoside triphosphates include deoxyribonucleoside triphosphates such as the four common deoxyribonucleoside triphosphates dATP, dCTP, dGTP and dTTP and ribonucleoside triphosphates such as the four common triphosphates rATP, rCTP, rGTP and rUTP.

The term "nucleoside triphosphates" also includes derivatives and analogs thereof, which are exemplified by those derivatives that are recognized and polymerized in a similar manner to the underivatized nucleoside triphosphates.

Nucleotide—a base-sugar-phosphate combination that is the monomeric unit of nucleic acid polymers, i.e., DNA and RNA. The term "nucleotide" as used herein includes modified nucleotides as defined below.

DNA—deoxyribonucleic acid.

RNA—ribonucleic acid. cDNA—a DNA copy of a corresponding RNA. It can be a sequence of DNA obtained by reverse transcription of an RNA molecule. It can include double-stranded or single stranded DNA obtained by amplification. An example, by way of illustration and not limitation, is the double-stranded DNA product obtained by PCR amplification of a bacterial plasmid insert. The DNA sequence inserted in the plasmid is previously obtained from reverse transcription of the corresponding RNA.

Modified nucleotide—a unit in a nucleic acid polymer that contains a modified base, sugar or phosphate group. The modified nucleotide can be produced by a chemical modification of the nucleotide either as part of the nucleic acid polymer or prior to the incorporation of the modified nucleotide into the nucleic acid polymer. For example, the methods mentioned above for the synthesis of an oligonucleotide may be employed. In another approach a modified nucleotide can be produced by incorporating a modified nucleoside triphosphate into the polymer chain during an amplification reaction. Examples of modified nucleotides, by way of illustration and not limitation, include dideoxynucleotides, derivatives or analogs that are biotinylated, amine modified, alkylated, fluorophor-labeled, and the like and also include phosphorothioate, ring atom modified derivatives, and so forth.

Nucleoside—is a base-sugar combination or a nucleotide lacking a phosphate moiety.

Analyte—a molecule of interest, which may be a molecule found directly in a sample such as biological tissue, including body fluids, from a host. The term "analyte" includes ligands and receptors as defined above. Particular examples of analytes include antibodies, antigens, haptens, oligonucleotide probes, polynucleotides, peptides, proteins, enzymes, and so forth. The sample can be examined directly or may be pretreated to render the analyte more readily detectable. The biological tissue includes excised tissue from an organ or other body part of a host and body fluids, for example, urine, blood, plasma, serum, saliva, semen, stool, sputum, cerebral spinal fluid, tears, mucus, and the like.

Ancillary Materials—various ancillary materials will frequently be employed in methods for determining an analyte using compounds prepared in accordance with the present invention. For example, buffers will normally be present in an assay medium, as well as stabilizers for the assay medium and the assay components. Frequently, in addition to these additives, proteins may be included, such as albumins; organic solvents such as formamide; quaternary ammonium salts; polyanions such as dextran sulfate; surfactants, particularly non-ionic surfactants; binding enhancers, e.g., polyalkylene glycols; or the like.

DETAILED DESCRIPTION OF THE INVENTION

The present invention allows the production of surfaces that contain linking groups for linking to monomers, oligomers and polymers. The linking group is a chain that has a hydrophobic part that facilitates attachment of the linking chain to the surface, which is usually hydrophobic. The linking chain also has a hydrophilic portion to assist in the ability of molecules, e.g., oligonucleotides or polynucleotides that are linked to the surface through the linking chain, to bind to their specific binding partners, e.g., to complementary molecules.

In its broadest application the present invention is directed to a method for producing surfaces which have uniform and reproducible linking group densities. A surface is employed that comprises a linking group consisting of a first portion comprising a hydrocarbon chain, optionally substituted, and a second portion comprising an alkylene oxide or an alkylene imine wherein the alkylene is optionally substituted. One end of the first portion is attached to the surface and one end of the second portion is attached to the other end of the first portion by means of an amine or an oxy functionality. The second portion terminates in an amine or a hydroxy functionality. The present invention may be used for immobilizing a substance to a surface. The surface is reacted with the substance to be immobilized under conditions for attachment of the substance to the surface through the intermediacy of the linking group.

The production of the surfaces in accordance with the present invention may be accomplished so that the number of features present on the surface can be reproduced consistently. Thus, batch to batch variability that is a problem in prior art processes is avoided in the present invention. The present invention provides a modular reaction system, which allows flexibility and permits in situ synthesis of polynucleotides as well as attachment of whole polynucleotides such as oligonucleotides and cDNA to surfaces. Flexibility is also realized in the chemical composition, length of the linking group and in the density of the linking group that may be applied to a surface. The present invention is a platform on which a wide variety of applications can be realized. The invention herein permits controlled surface energy that is a very important parameter in in situ synthesis of polynucleotides. The invention permits controlled attachment densities of whole polynucleotides such as oligonucleotides and cDNA that may have different density requirements for optimum hybridization performance. It also permits control of non-specific binding, which is important to optimum detection of analytes in assays.

In one embodiment of the present invention, the alkylene oxide is a polyoxyalkylene chain represented by the formula:

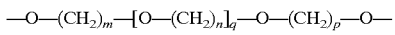
—O—(CH$_2$)$_m$—[O—(CH$_2$)$_n$]$_q$—O—(CH$_2$)$_p$—O— wherein m, n and p are each independently an integer of 1 to about 4, preferably, m=n=p=2, and q is an integer of 1 to about 24, preferably 1 to about 10, more preferably 1 to about 4, even more preferably 2.

In another embodiment the alkylene imine is a polyiminoalkylene chain represented by the formula:

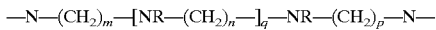
—N—(CH$_2$)$_m$—[NR—(CH$_2$)$_n$—]$_q$—NR—(CH$_2$)$_p$—N— wherein R is H or alkyl, m, n, and p are each independently an integer of 1 to about 4, preferably, m=n=p=2 and q is an integer of 1 to about 24, preferably 1 to about 10, more preferably 1 to about 4, even more preferably 2.

Usually, the substance to be linked is combined in a suitable medium with a surface, which comprises all or the first portion of the linking group. The medium may be a protic solvent or an aprotic solvent. Usually, it is desirable to conduct reactions in a protic solvent because of the nature of the ligands, receptors and surfaces involved. The medium may be an aqueous medium that is solely water, a buffer, or that contains from about 0.01 to about 80 or more volume percent of a cosolvent such as an organic solvent. Such organic solvents include by way of illustration and not limitation oxygenated organic solvents of from 1 to about 6, more usually from 1 to about 4, carbon atoms, including alcohols such as methanol, ethanol, propanol, etc., ethers such as tetrahydrofuran, ethyl ether, propyl ether, etc., dimethylformamide, dimethylsulfoxide, and the like. Other co-solvents may be detergents including, by way of illustration and not limitation, Triton®, sodium dodecyl sulfate and the like. Usually these cosolvents, if used, are present in less than about 70 weight percent, more usually in less than about 30 weight percent.

The pH for the medium will usually be in the range of about 5 to about 13, more usually in the range of about 6 to about 12, and preferably in the range of about 7 to about 11. The pH is generally selected to achieve optimum reaction between the molecules containing the moieties. Among the factors that must be considered are the pH dependence of the reactive molecules, concentration of reactive molecules, energy of activation and so forth. Various buffers may be used to achieve the desired pH and maintain the pH during the reaction. Illustrative buffers include acetate, borate, phosphate, carbonate, tris, citrate, barbital, various mixtures thereof and the like. The particular buffer or solvent employed is not critical to this invention, but in an individual reaction one or another buffer may be preferred.

The conditions are sufficient to permit the formation of a product of the reaction of the first and second reagents wherein M1 becomes conjugated to the second reagent. Moderate temperatures are normally employed for carrying out reactions in accordance with the present invention, preferably, room temperature. The temperature is usually in the range of from about 0° to about 90° C., more usually from about 10 to about 60° C., preferably, about 20 to about 45° C. Higher or lower temperatures are employed where appropriate.

The amount of the reagents employed in the method of the present invention is dependent on the nature of the reagents, solubility of the reagents, reactivity of the reagents, availability of the reagents, purity of the reagents, and so forth. Such amounts should be readily apparent to those skilled in the art. Usually, stoichiometric amounts are employed, but excess of one reagent over the other may be used where circumstances dictate. Typically, the amounts of the reagents are those necessary to achieve the result desired in accordance with the present invention.

The time period for conducting the present method is dependent upon the specific reaction and reagents being utilized. Examples, by way of illustration and not limitation are: reaction with hydroxyl-terminated surfaces with phosphoramidites can be complete in seconds; reaction of amine-terminated surfaces with acid anhydrides or acid chlorides can require minutes; reaction of surfaces terminated by activated esters with amine containing biopolymers can require hours.

The surface is reacted with the substance to be immobilized under conditions for attachment of the substance to the surface through the intermediacy of the linking group. As mentioned above, the surface may comprise all or only the first portion of the linking group. As will be understood, then, the linking group may be preformed on the surface or the first portion of the linking group may be preformed. Thus, the present invention provides for a modular synthesis. The preformed first portion will be discussed next since it also comprises the initial step in the preparation of the surface with both the first and second portions of the linking group thereon.

A surface is treated to attach the first portion, namely, the hydrocarbon chain, of the linking group. Preferably, the surface is siliceous, i.e., comprises silicon oxide groups, either present in the natural state, e.g., glass, silica, silicon with an oxide layer, etc., or introduced by techniques well known in the art. One technique for introducing siloxyl groups onto the surface involves reactive hydrophilic moieties on the surface. These moieties are typically epoxide groups, carboxyl groups, thiol groups, and/or substituted or unsubstituted amino groups as well as functionality that may be used to introduce such a group such as, for example, an olefin that may be converted to a hydroxyl group by means well known in the art. One approach involves introducing the silyl groups as part of the reagent that comprises the linking group or the first portion thereof as discussed more in detail below. Another approach is disclosed in U.S. Pat. No. 5,474,796 (Brennan), the relevant portions of which are incorporated herein by reference.

One procedure for the derivatization of a metal oxide surface uses an aminoalkyl silane derivative, e.g., trialkoxy 3-aminopropylsilane such as aminopropyltriethoxy silane (APS), 4-aminobutyltrimethoxysilane, 4-aminobutyltriethoxysilane, 2-aminoethyltriethoxysilane, and the like. APS reacts readily with the oxide and/or siloxyl groups on metal and silicon surfaces. APS provides primary amine groups that may be used to carry out the present methods. Such a derivatization procedure is described in EP 0 173 356 B1, the relevant portions of which are incorporated herein by reference. While this represents one of the preferred approaches, a variety of other attachment reactions are possible for both the covalent and non-covalent attachment as mentioned above.

The substrate or support comprising the hydrophilic reactive surface is combined with a composition that comprises the first portion of the linking group or hydrophobic portion. The reaction may be depicted as follows:

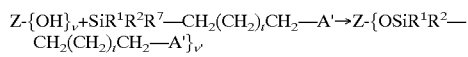

Z is a surface. At least one of $R^1$, $R^2$ and $R^7$ is a functionality reactive with the functionality on the surface, e.g., hydroxyl group, and the remaining are independently selected from the group consisting of functionalities reactive either with themselves or with the functionality on the surface or are non-reactive; alkyl, aryl, alkoxy, aryloxy, halogen and the like. At least one of $R^1$, $R^2$ and $R^7$ is usually a leaving group that enables binding of the silanes to the surface. These leaving groups are typically hydrolyzable so as to form a silyl ether linkage to the hydroxyl groups on the surface. Examples of suitable leaving groups include, but are not limited to, halogen atoms, particularly chloro, and alkoxy moieties, particularly lower alkoxy moieties. Preferably, the silyl functionality is a trichlorosilyl functionality, a tri(lower) alkoxysilyl functionality such as trimethoxysilyl or triethoxysilyl, mixed functionalities such as diisopropylchlorosilyl, dimethylchlorosilyl, ethyldichlorosilyl, methyl-ethylchlorosilyl or the like. For most surfaces v and v' are independently an integer of 1 to about $1 \times 10^7$ per square micron, wherein v is usually greater than v' and v and v' are independently at least about 10 per square micron, usually at least about $10^2$, more usually about $10^3$ to about $5 \times 10^6$, commonly, about $10^4$ to about $10^7$ and t is an integer of about 4 to about 38, usually, about 4 to about 18, more usually, about 6 to about 12. A' is a leaving group that may be protected with a protecting group.

The above product, which comprises the surface functionalized with the hydrophobic first portion of the linking group, may be used in a reagent system for preparing the surface to which the substance in question is attached. In this regard the above surface may be combined with a second composition that is a hydrophilic reagent that comprises the second portion of the linking group. The combination is treated under conditions sufficient to permit the second composition to attach to the first composition and, where the substance is included in the combination, to permit the substance to attach to the second composition. The reaction may be depicted as follows:

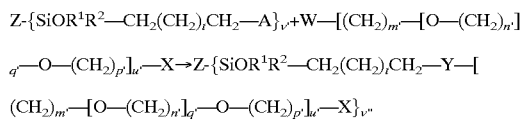

Z is a surface. $R^1$ and $R^2$ are independently selected from the group consisting of alkyl, aryl, alkoxy, aryloxy, halogen and the like; v' and v" are independently an integer of 1 to about $1 \times 10^7$ per square micron, wherein v' is usually greater than v" and v' and v" are independently at least 10 per square micron, usually at least about $10^2$, more usually about $10^3$ to about $5 \times 10^6$, commonly, about $10^4$ to about $10^6$, and t is an integer of about 4 to about 38, usually, about 4 to about 18, more usually, about 6 to about 12. A is an unprotected leaving group, and m', n', and p' are each independently integers of 1 to about 4, preferably m'=n'=p'=2 and q' is an integer of 1 to about 24, preferably 1 to about 10, more preferably 1 to about 4, and u' is an integer of 1 to about 3. W is OH or $NHR^6$ wherein $R^6$ is H or alkyl. X is OH, $NR^4R^5$ wherein $R^4$ and $R^5$ are each independently H or alkyl or L'—D' wherein L' is a linking group or a bond and D' is a substance, such as a ligand or a receptor, to be attached to the surface.

The conditions for the reaction of the leaving group A with W depends on the nature of A and W. For example, where A is halo and W is $NH_2$, the reagents are heated at a temperature of from about 60° to about 120° C., more usually from about 95° to about 110° C., for a period of time of from about 30 min to about 24 hours, more usually, from about 8 hours to about 16 hours (overnight). Under these conditions the halogen is displaced by the nitrogen of the amine group to form a secondary amine linkage. Reaction conditions will be apparent to those skilled in the art for other A groups with as $NH_2$, which include, by way of example but not limitation, tosyl, azido, nitrile, triflate, imadazoyl, triazolyl, triphenylphosphine oxide, and the like.

Where A is halo and W is OH, the reagents are combined in a suitable medium with a strong base such as sodium hydride, lithium aluminum hydride, sodium metal, butyl lithium, t-butyl lithium, or the like. The reagents are heated at a temperature of from about 40° to about 110° C., more usually from about 60° to about 90° C., for a period of time of from about 15 minutes to about 4 hours, more usually, from about 30 minutes to about 2 hours. Under these conditions the halogen is displaced by the oxygen of the hydroxyl group to form the ether linkage. Reaction conditions will be apparent to those skilled in the art for other A groups with W as OH, which include, by way of example and not limitation, tosyl, azido, nitrile, triflate, imadazoyl, triazolyl, triphenylphosphine oxide, and the like.

Where neither of $R^4$ and $R^5$ is L'-D', the product of the reaction may be employed in a reaction to attach a substance to the surface through the intermediacy of the linking group. In one embodiment the OH or $NR^4R^5$ group of the reagent is used to attach the substance, which comprises, or is treated to comprise, an amine specific reactive functionality or an alcohol specific reactive functionality. This functionality may be directly bonded to the substance or it may be bonded to a linking group that is attached to the substance. Conditions such as temperature, pH and time of the reaction depend on the particular functionality employed. Such conditions are generally known in the art.

In another approach that is applicable particularly to some substances, usually, polymeric substances such as polynucleotides, e.g., cDNA, double stranded DNA, etc., the polynucleotide is applied to the surface of the above reagent by spotting, using pipettes, pins, inkjets, or the like. The surface is irradiated with UV light and the substance becomes covalently attached to the linking group, presumably, by non-specific, free-radical cross-linking. The irradiation procedure employed is similar to that used with surfaces that have been pretreated with polylysine, or aminopropyltriethoxysilane, and the like. Usually, the surface is irradiated with light, such as UV light, for a period of time that allows an energy transfer from about 200 millijoule to about 20000 millijoule, usually, from about 4500 to about 18000 millijoule, at a wavelength of from about 190 mn to about 400 nm, usually, from about 200 nm to about 300 nm.

In another example entire polynucleotides may be attached to the linking group by employing a polynucleotide reagent that has an appropriate amine specific, thiol specific, azide specific, diels-alder specific, metal-coordination specific, or alcohol specific reactive functional group. Methods for introducing such functional groups into a polynucleotide include incorporation of modified nucleotides by enzymatic reaction; the use of modified nucleotide monomers during chemical synthesis of oligonucleotides; or by reaction with chemical modifying reagents on polynucleotides either during or after synthesis; these techniques are well-know to those skilled in the art.

In another approach the substance attached to the linking group on the surface is a nucleoside or nucleotide. Methods for introducing appropriate amine specific or alcohol specific reactive functional groups into a nucleoside or nucleotide include and are not limited to, addition of a spacer amine containing phosphoramidites, addition on the base of alkynes or alkenes using palladium mediated coupling, addition of spacer amine containing activated carbonyl esters, addition of boron conjugates, formation of Schiff bases.

After the introduction of the nucleoside or nucleotide onto the surface, the attached nucleotide may be used to construct the polynucleotide by means well known in the art. For example, in the synthesis of arrays of oligonucleotides, nucleoside monomers are generally employed. In this embodiment an array of the above compounds is attached to the surface and each compound is reacted to attach a nucleoside. Nucleoside monomers are used to form the polynucleotides usually by phosphate coupling, either direct phosphate coupling or coupling using a phosphate precursor such as a phosphite coupling. Such coupling thus includes the use of amidite (phosphoramidite), phosphodiester, phosphotriester, H-phosphonate, phosphite halide, and the like coupling. One preferred coupling method is the phosphoramidite coupling, which is a phosphite coupling. In using this coupling method, after the phosphite coupling is complete, the resulting phosphite is oxidized to a phosphate. Oxidation can be effected with iodine to give phosphates or with sulfur to give phosphorothioates. The phosphoramidites are dissolved in anhydrous acetonitrile to give a solution having a given ratio of amidite concentrations. The mixture of known chemically compatible monomers is reacted to a solid support, or further along, may be reacted to a growing chain of monomer units. In one particular example, the terminal 5'-hydroxyl group is caused to react with a deoxyribonucleoside-3'—O—(N,N-diisopropylamino) phosphoramidite protected at the 5'-position with dimethoxytrityl or the like. The 5' protecting group is removed after the coupling reaction, and the procedure is repeated with additional protected nucleotides until synthesis of the desired polynucleotide is complete. For a more detailed discussion of the chemistry involved in the above synthetic approaches, see, for example, U.S. Pat. No. 5,436,327 at column 2, line 34, to column 4, line 36, which is incorporated herein by reference in its entirety.

Where one of $R^4$ and $R^5$ is L'—D', the product is the ultimate product desired, namely, the substance attached to the surface through the intermediacy of the linking group. In this circumstance the second reagent comprises the second portion of the linking group to which the substance is already attached. Such attachment may be carried out in a manner similar to the attachment of the substance to the second portion of the linking group as described above.

As mentioned earlier, the oligonucleotide arrays may be used to carry out nucleic acid hybridization in a diagnostic fashion. To this end the array is exposed to a solution containing polynucleotide analytes in the usual manner and labeled DNA fragments selectively hybridize at sites where a complementary oligonucleotide is found. Other approaches utilizing the oligonucleotide arrays produced in accordance with the present invention will be apparent to those skilled in the art.

The alkylene oxide reagent or the alkylene imine reagent may be prepared by methods that are well known to one skilled in art. The alkylene oxide or alkylene imine precursor is readily available or readily synthesized.

A particular embodiment of the present invention is depicted in FIG. 1 by way of illustration and not limitation. A glass surface is shown with pendant hydroxyl groups. The glass surface is treated with $BrCH_2(CH_2)_9CH_2SiCl_3$ or $BrCH_2(CH_2)_9CH_2SiOMe_3$ under conditions for the formation of a silyl ether bond between the hydroxyl groups on the glass surface and the Si group of the alkyl reagent. The alkylsiloxy surface is then treated with an alkylene oxide reagent under conditions to introduce the alkylene chain into the alkyl portion of the linking group on the glass surface. The alkylene oxide or alkylene imine reagent has the formula W'—$(CH_2)_3$—O—$(CH_2)_2$—O—$(CH_2)_2$—O—$(CH_2)_3$—W' wherein W' is $NH_2$ or the formula W'—$(CH_2)_3$—O—$(CH_2)_2$—O—$(CH_2)_2$—O—$(CH_2)_3$—X' wherein W' is $NH_2$ or OH and X' is $NH_2$ or OH depending on the linking group desired on the surface.

Figure 2:
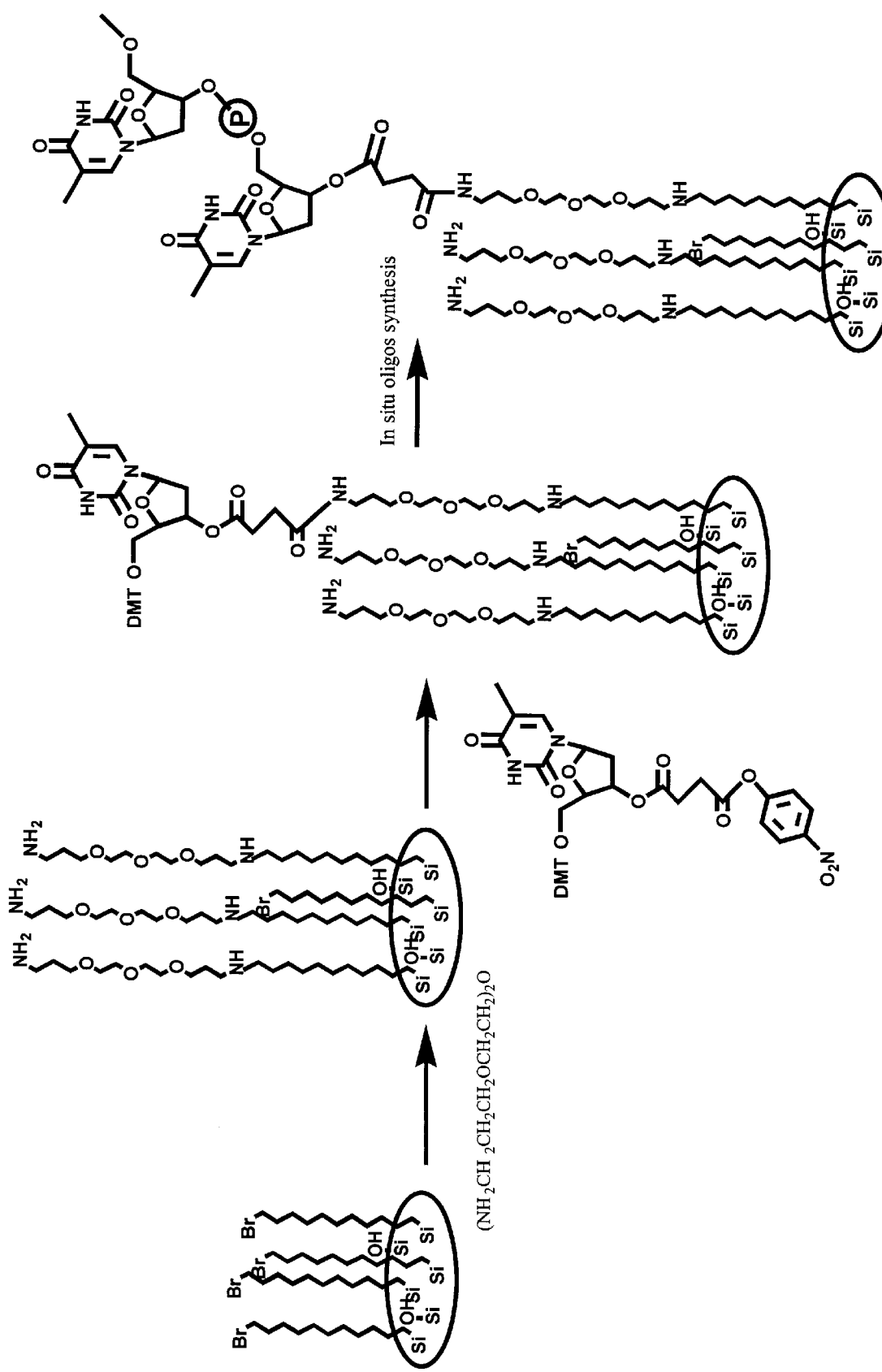
FIG. 2 is a schematic depicting another aspect of the present invention.

Another particular embodiment of the present invention is depicted in FIG. 2 by way of illustration and not limitation. A glass surface is shown with pendant bromoalkyl groups, having been prepared as discussed above. The glass surface is treated with an alkylene oxide reagent under conditions to introduce the alkylene chain into the alkyl portion of the linking group on the glass surface. The alkylene oxide reagent has the formula: $(NH_2CH_2CH_2OCH_2CH_2)_2O$. The glass surface is contacted with a medium containing the p-nitrophenyl ester activated protected nucleoside reagent under conditions for the amide formation between the terminal amine group of the linking group and the p-nitrophenyl ester of the nucleoside reagent. The attached nucleoside is then used to form a polynucleotide in situ. In this particular embodiment the nucleoside reagent can also comprise a succinate linkage. This linkage is basolabile and permits cleavage of the link to the surface. As a result the synthesized polynucleotide may be subjected to analysis such as, e.g., high pressure liquid chromatography (BPLC) analysis. Furthermore, the linker may be quantitated by, for example, reaction with fluorescein isothiocyanate prior to synthesis of the polynucleotide. In this way the number of linking groups present on the surface may be determined. This is an important feature of the present invention because it is often extremely important to be able to monitor the extent of the addition of linking groups to the surface. This is particularly important where the resulting surfaces are used in quantitative determinations of polynucleotide analytes.

Other labile groups may be used in place of a succinate linkage to yield a cleavable moiety. Suitable cleavable sites include, but are not limited to, base-cleavable sites such as esters, particularly succinates (as mentioned above) (cleavable by, e.g., ammonia or trimethylamine), quatemary ammonium salts (cleavable by, e.g., aqueous sodium hydroxide), acid-cleavable sites such as, e.g., benzyl alcohol derivatives (cleavable using trifluoroacetic acid), teicoplanin aglycone (cleavable by trifluoroacetic acid followed by base), acetals and thioacetals (cleavable by trifluoroacetic acid), thioethers (cleavable, e.g., by HF or cresol) and sulfonyls (cleavable by trifluoromethane sulfonic acid, trifluoroacetic acid, thioanisole, or the like); nucleophile-cleavable sites such as phthalamide (cleavable with substituted hydrazines), ester (cleavable with ,e.g., aluminum trichloride) and Weinreb amide (cleavable with lithium aluminum hydride) and other types of chemically cleavable sites, including phosphorothioate (cleavable with silver or mercuric ions) and diisopropyldialkoxysilyl (cleavable with fluoride ion). Other cleavable sites will be apparent to one skilled in the art such as those disclosed in, for example, Brown, *Contemporary Organic Synthesis* (1997) 4(3):216–237.

Figure 3:
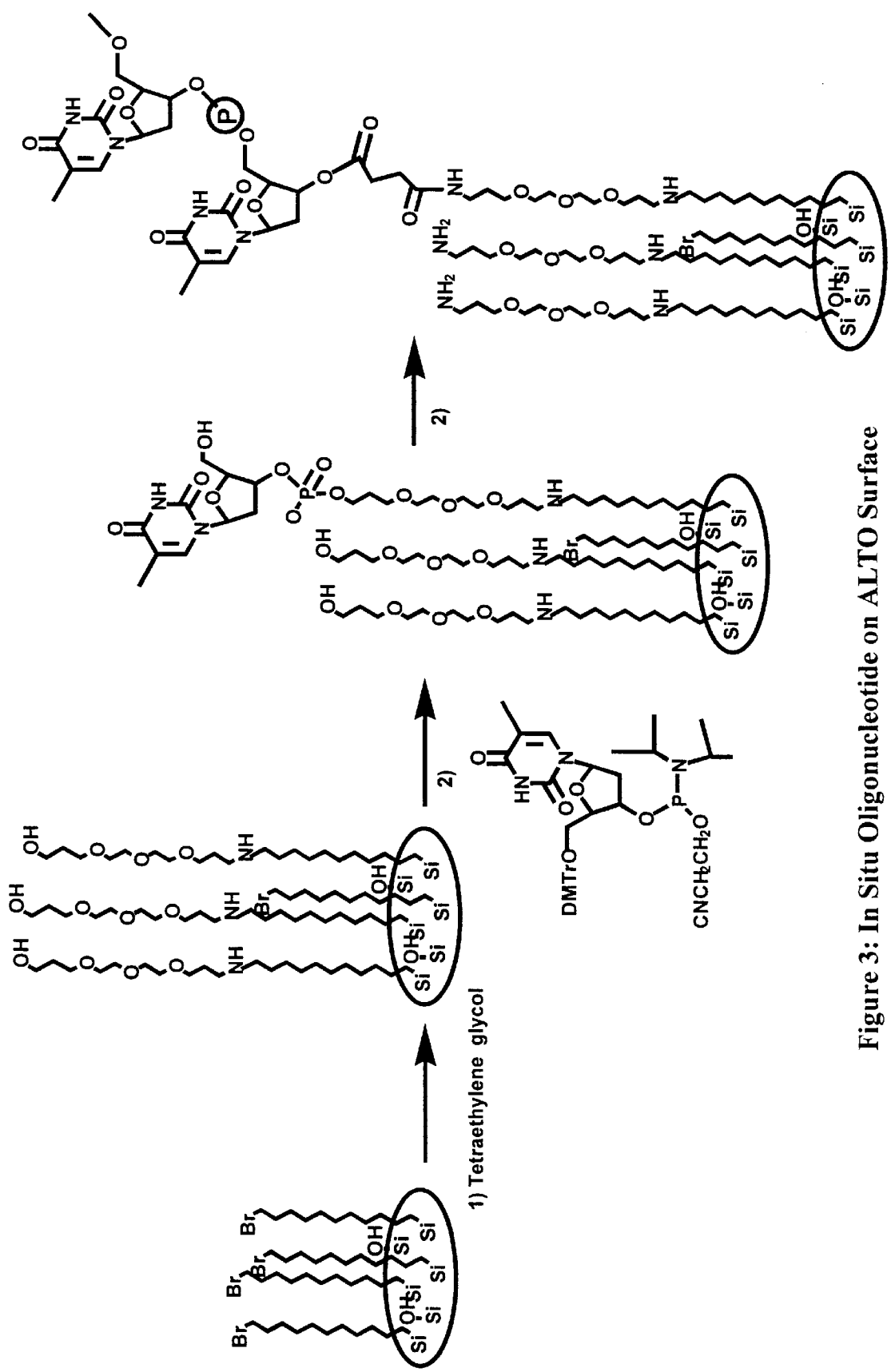
FIG. 3 is a schematic diagram depicting another aspect of the present invention.

Another approach is depicted in FIG. 3 by way of illustration and not limitation. A glass surface is shown with pendant bromoalkyl groups, having been prepared a discussed above. The glass surface is treated with an alkylene oxide reagent under conditions to introduce the alkylene chain into the alkyl portion of the linking group on the glass surface. The alkylene oxide reagent has the formula: $(NH_2CH_2CH_2CH_2OCH_2CH_2)_2O$. The glass surface is contacted with a medium containing the protected nucleoside phosphoramidite reagent under conditions for the attachment of the nucleoside to the terminal carbon atom of the linking group. The linking group utilized in this particular embodiment is stable under basic conditions required to deprotect the nucleotides after in situ synthesis of the polynucleotide. The attached nucleoside is then used to form a polynucleotide in situ. In this particular embodiment the linker may be quantitated by, for example, reaction of the hydroxyl functions with Cy3 phosphoramidite and by photo-spectroscopic measurement of Cy3 conjugate with the surface.

One consideration in the above synthesis is the control of the addition of the alkylene oxide reagent to the alkyl chain on the surface, which is in competition with hydrolysis. Control of the addition of this reagent may be achieved by complete dryness of the reagent, of the substrates and of the solvent. Control of the reaction is also achieved by stoichiometric control of the reagents, which is done in a large excess of the alkylene oxide.

Another consideration in the above synthesis is the control of the density of the linking group. Control of the density can be achieved by mixing two silanes: one containing a terminal reactive functionality as a halo group for example and the other silane being terminated by a non reactive group such as an alkyl or alkoxy group, for example, so that the density is controlled only by the density of the silane containing the terminal reactive. Another way to control the density of the linker is to control the addition of the second portion of the linker e.g. by using a mixture of akylene oxide having two hydroxyl at each terminal with an alkylene oxide containing only one hydroxyl at one terminus and a non-reactive functionality at the second terminus such as a alkyl group. In the case of alkylene diamine, the control of the reaction can be achieved by changing the concentration of the reagent (from neat to about 5%).

Another important consideration with respect to all of the linking groups employed is the resulting surface contact angle of a droplet of the solution of a substance to be attached by the linking group. By the term "contact angle" is meant the angle between the surface and a beaded droplet at the point where it contacts the surface. Control of the contact angle of the linking group may be achieved by chemical composition of the surface such as by the use of hydrophilic or hydrophobic silanes. Contact angle may also be changed when applicable by change of the composition of the depositing solution. Addition of detergent, organic solvent or change in ionic strength of a buffer may contribute to better control of deposition onto the surface.

In addition to the procedures discussed above for preparing surfaces to which nucleotides, nucleosides and polynucleotides are attached, the surface functionalized with the hydrophobic first portion of the linking group may be used in a reagent system for preparing a surface to which any substance in question is attached or on which any substance is synthesized. Thus, the above surface may be used in any of a number of known chemical and biological procedures other than in the solid phase chemical synthesis of polynucleotides or attachment of polynucleotides to a surface. Such procedures include synthesis of oligosaccharides, oligopeptides, etc. attachment of ligands and receptors to surfaces, and so forth. In this regard the above surface may be combined with a second composition that is a hydrophilic reagent that comprises the second portion of the linking group. The combination is treated under conditions sufficient to permit the second composition to attach to the first composition. The second composition may include the substance to be attached to the surface or, alternatively, it may comprise a monomer as the starting point for synthesis of an oligomer.

The present reagent system may be used, for example, to synthesize polypeptides. This approach comprises attaching a first amino acid to the terminal portion of the linking group on the surface. The synthesis involves sequential addition of carboxyl-protected amino acids to a growing peptide chain with each additional amino acid in the sequence similarly protected and coupled to the terminal amino acid of the oligopeptide under conditions suitable for forming an amide linkage. Such conditions are well known to the skilled artisan. See, for example, Merrifield, B. (1986), Solid Phase Synthesis, *Sciences* 232, 341–347. After polypeptide synthesis is complete, acid is used to remove the remaining tenninal protecting groups. The support bound polypeptides thus provided can then be used in any number of ways, e.g., in screening procedures involved in combinatorial processes, in chromatographic methods, and the like.

Alternatively, as mentioned above for polynucleotides, the method and reagents of the present invention may be used to provide oligomers bound to a support by means of a chemically cleavable site. Thus, in accordance with this embodiment oligopeptides and polypeptides may be cleaved from the surface where a cleavable site was introduced into the molecule as described above. The cleavable site may be incorporated so that, upon cleavage, the free terminus of the linking group is then used for solid phase synthesis. Alternatively, the cleavable site may be incorporated to allow the synthesized polymer to be removed from the surface. Other ways of utilizing this particular aspect of the present invention will be suggested to those skilled in the art in light of the teaching herein.

The present invention may be used to bind specific binding pair members such as an antigen, hapten, antibody, biotin, avidin, nucleic acids and so forth to a support for use in diagnostic assays for the determination of an analyte. Molecules attached to a surface in accordance with the present invention may be used in any assay for an analyte in a manner in which a surface-bound reagent is employed. A solid phase reagent produced in accordance with the present invention can be adapted to most assays involving specific binding pair members such as ligand-receptor, e.g., antigen-antibody reactions, polynucleotide binding assays, and so forth. The assays may be homogeneous or heterogeneous, usually heterogeneous, including competitive and sandwich. In a specific binding assay, the sample may be pretreated, if necessary, to remove unwanted materials.

In the heterogeneous approach the reagents are usually the sample, a specific binding pair member such as an antibody, and means for producing a detectable signal. One of the reagents is attached to the surface of a support, such as a microtiter plate or slide, paper strip, and so forth in a manner as described above for attaching substances to surfaces. The support is contacted with the specific binding pair member in an aqueous phase. The support is then separated from the liquid phase and either the support phase or the liquid phase is examined for a detectable signal employing means for producing such signal, which includes a label. Exemplary of heterogeneous assays are the radioimmunoassay (RIA), immunofluorescence methods, enzyme-linked immunoassays, such as the enzyme-linked immunosorbent assay (ELISA, see U.S. Pat. Nos. 3,654,090; 3,839,153; 3,850,752; 4,016,043 and Re 29,169, the disclosures of which are incorporated herein by reference).

Enzyme immunoassays (EIA's) comprise quantitative procedures in which a specific binding reaction such as, in immunological cases, the antigen-antibody reaction is monitored by enzyme activity measurements. The term ELISA is generally used for reagent excess assays of specific antibodies or antigens. However, sometimes, it is used interchangeably with EIA and immunoenzymometric assay. There are two basic types of EIA's: heterogeneous (separation required) and homogeneous (separation free) assays. In the heterogeneous systems, since the activity of the enzyme label is not affected by the antigen-antibody reaction, it must be separated into antibody-bound and free, unbound enzyme fractions. The enzyme activity of either of these two fractions can be measured. In the homogeneous systems, the enzyme activity of the assay solution is measured without a prior physical separation of the antibody-bound enzyme label from the free, unbound one, primarily because the activity of the bound enzyme label is significantly different from the unbound one. The various heterogeneous and homogeneous EIA's can be further characterized as either competitive or non-competitive (inununoenzymometric) assays, depending on whether the unlabeled antigen and the antigen linked to an enzyme or attached to a solid phase compete for a limited number of antibody binding sites, or whether the antigen or antibody to be measured is allowed to react alone with an excess of immune reactant. For a more detailed discussion of various enzyme assay techniques, see "Enzyme Immunoassay" by Edward T. Maggio, CRC Press, Inc., Boca Raton, Fla., 1980. See also, for example, U.S. Pat. Nos. 3,690,834; 3,791,932; 3,850,578; 3,853,987; 3,867,517; 3,901,654; 3,935,074; 3,984,533; 3,996,345 and 4,098,876, which listing is not intended to be exhaustive.

One or more of the above compositions of the reagent system may be provided as a kit in packaged combination with one another or with reagents for conducting an assay. To enhance the versatility of the subject invention, the reagents can be provided in the same or separate containers so that the ratio of the reagents provides for substantial optimization of the method or assay. The reagents may each be in separate containers or various reagents can be combined in one or more containers depending on the cross-reactivity and stability of the reagents.

The kit can further include other separately packaged reagents for conducting an assay such as enzyme substrates, additional sbp members, ancillary reagents and so forth. The relative amounts of the various reagents in the kits can be varied widely to provide for concentrations of the reagents that substantially optimize the reactions that need to occur during the present method and to further substantially optimize the sensitivity of the assay. The kit can further include a written description of a method in accordance with the present invention as described above.

EXAMPLES

The invention is demonstrated further by the following illustrative examples. Parts and percentages recited herein are by weight unless otherwise specified. Temperatures are in degrees centigrade (°C.). Unless indicated otherwise, chemicals were reagent grade and commercially available from sources such as Gibco (Rockville, Md.), Aldrich Chemical Company (Milwaukee, Wis.) and Sigma Chemical Company (St. Louis, Mo.). The following preparations and examples illustrate the invention but are not intended to limit its scope.

Example 1

1. Silylation of glass slides with 11-bromoundecyl trichlorosilane

Reagents: 11-Bromoundecyl trichlorosilane from Gelest Inc. (Tullytown, Pa.) ($Br(CH_2)_{10}CH_2SiCl_3$; catalog # SIB 1908.0). A reactor was taken out of a drying oven and quickly assembled. A boat containing 25 clean glass slides was placed into the reactor and purged with $N_2$ for 1 hour (hr). Into a 1000 ml freshly oven-dried bottle capped with a septum was cannulated 800 ml of anhydrous toluene, and 10 g of 11-bromoundecyl trichlorosilane was added via a syringe. The silane solution was swirled to mix the contents and transferred to the reactor via a cannula. The silylation was carried out at 100° C. for 2 hr under $N_2$ atmosphere. The silane solution was then cannulated out of the reactor and replaced with 800 ml of fresh anhydrous toluene. After 5 minutes of stirring, the boat containing the silylated slides was removed from the reactor and put into a fresh toluene wash. The boat was dipped up and down for about 50 times. The toluene was removed and 800 ml of acetonitrile was used as the next solvent wash. After. 50 dips, the acetonitrile was replaced with a fresh acetonitrile wash. The slides were dried with a stream of $N_2$, wrapped in aluminum foil and stored in a dry box.

Figure 4:
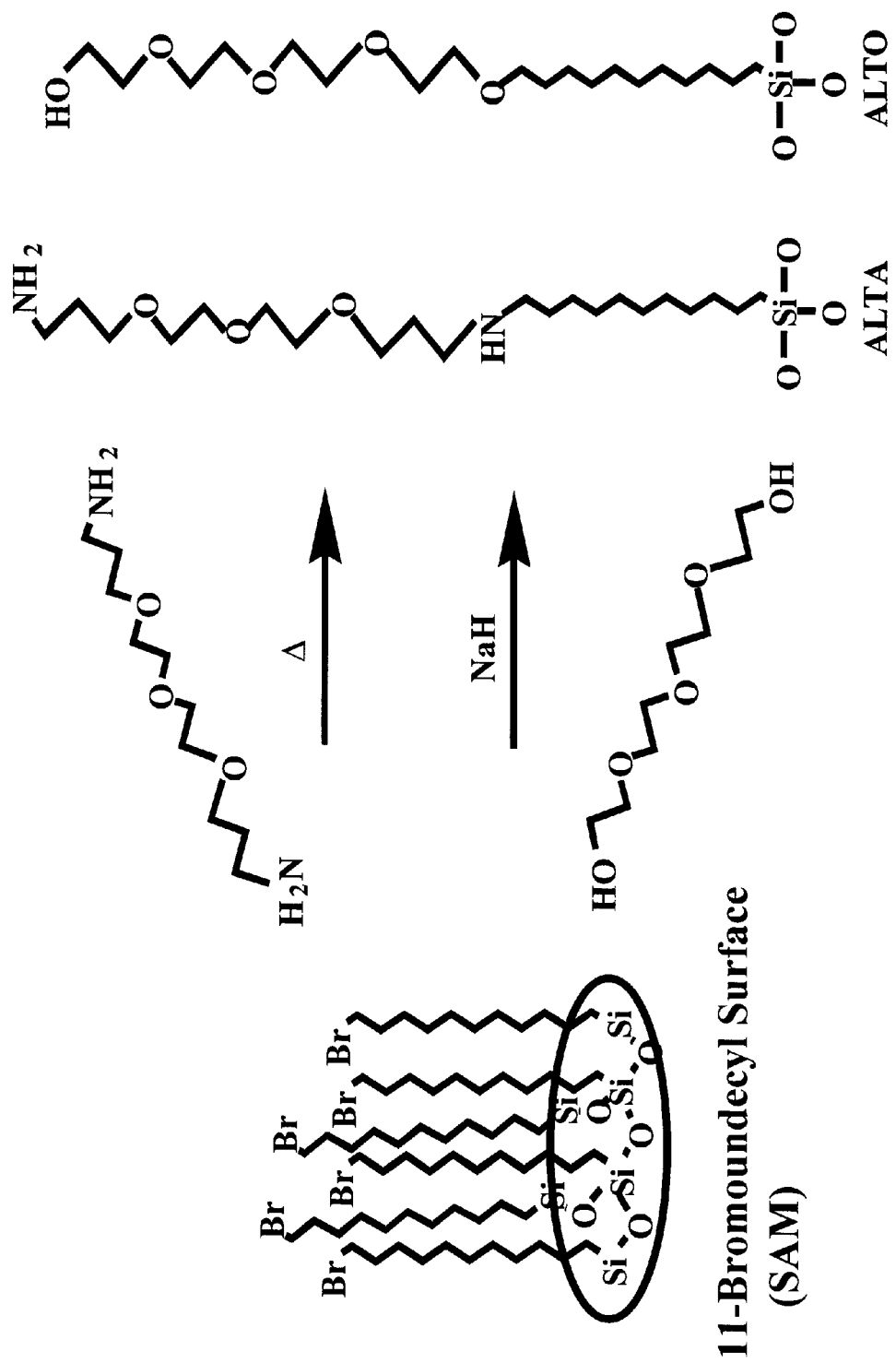
FIG. 4 is a schematic diagram depicting another aspect of the present invention.

2. Conversion of the 11-bromoundecylsilyloxy surface to a surface terminated with an amine functionality in accordance with the present invention (ALTA surface) (FIG. 4)

Reagents: 4,7,10-Trioxa-1,13-tridecanediamine from Aldrich ($NH_2CH_2CH_2CH_2OCH_2CH_2)_2O$; catalog # 36,951-9). Twenty five (25) obtained as described above in Example 1 were placed into a reactor. The reactor was filled with 800 ml of 4,7,10-Trioxa-1,13-tridecanediamine and heated to 100° C. The reactor containing the slides was placed into a jacketed reactor filled with 70% ethylene glycol in water as circulating solution. The reaction was kept at 100° C. overnight. After cooling down to room temperature, the slides were removed from the reactor and washed in a beaker by dipping the boat continuously up and down in the solvent wash successively with: dimethylformamide (DMF) (twice), acetonitrile (twice). The slides having an ALTA surface were dried with a stream of $N_2$, wrapped in aluminum foil and stored in a dry box.

Figure 5:
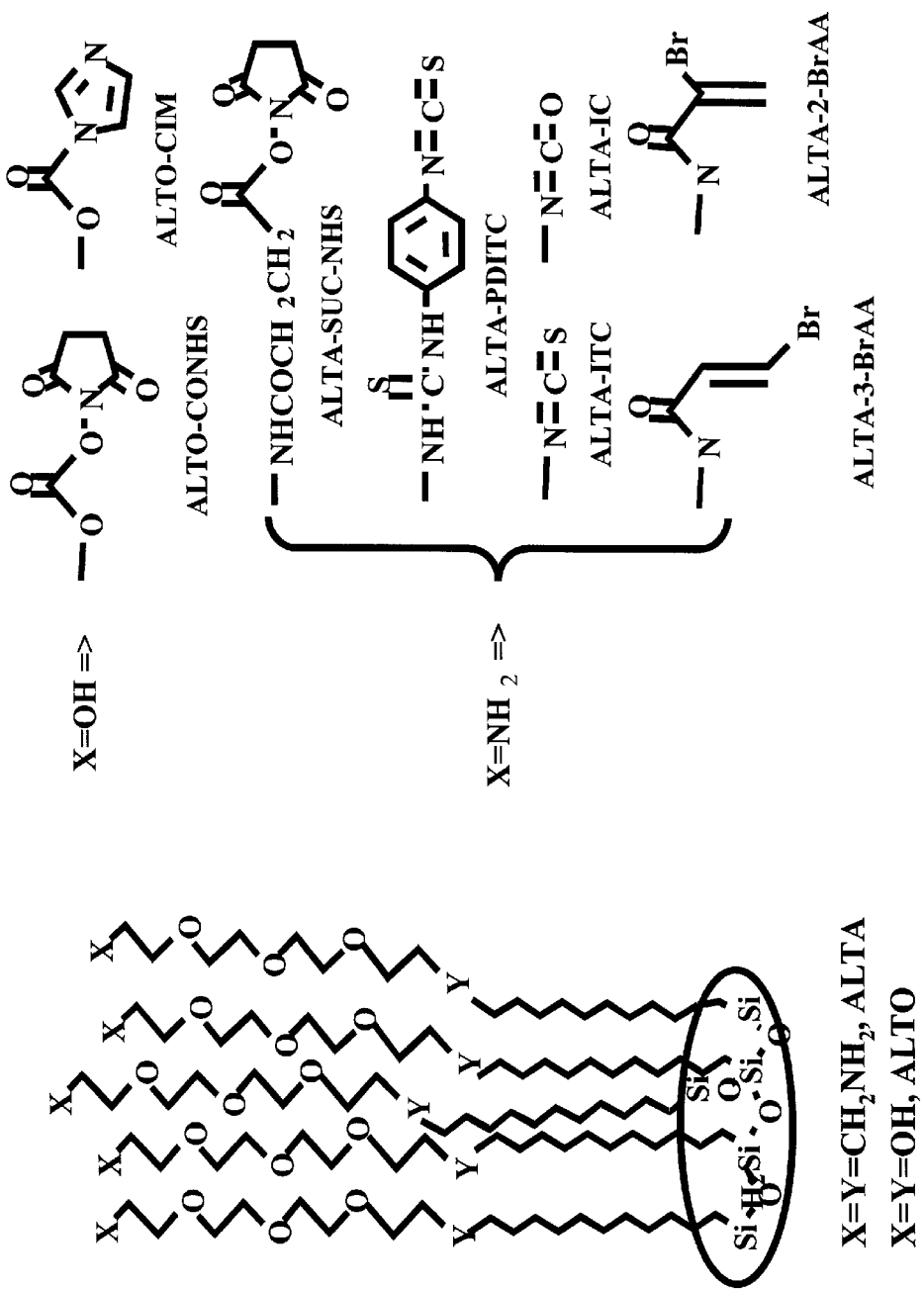
FIG. 5 is a schematic diagram depicting surfaces in accordance with the present invention.

3. General protocol for conversion of terminal amine functionality on surface of the slides of Example 2 (ALTA surface) to an amine-reactive functionality such as succinate N-hydroxysuccinimide (SUC-NHS), 1,4-phenylene-diisothiocyanate (PDITC), isocyanate (IC) and 3-bromoacrylate conjugate (3-BrAA) (FIG. 5)

The reaction was generally carried out under anhydrous conditions and required the use of dry material (reactor, cannula, and so forth) and anhydrous solvent. The reaction was conducted at room temperature, unless specified otherwise, in a 0.01M to 0.1M solution of reagent for several hours to overnight. The derivatized slides were then thoroughly washed in appropriate solvents and stored in a $N_2$ box.

4. Conversion of surface terminated with an amine functionality to a surface with a terminal 3-BrAA functionality The reactor was taken out of the drying oven and quickly assembled. The boat containing 25 slides from Example 2 above was placed into the reactor and purged with $N_2$. A 0.06 M solution of p-$NO_2$-phenyl(-3-bromo)acrylate (13.06 g) (Omega Chemicals Company, Quebec, Canada) in 800 ml of methylene chloride was transferred via a cannula to the reactor. The reaction was left overnight at room temperature, under stirring. The solution was then removed by cannula, and the slides were washed successively with $CH_2Cl_2$ (twice), methanol (MeOH), $H_2O$ and acetonitrile.

5. Conversion of surface terminated with an amine functionality to a surface terminated with a PDITC functionality Reagents: 1,4-phenylene diisothiocyanate from Aldrich: (PDITC, catalog # 26,224-2). Twenty five (25) slides prepared as described in Example 2 above (ALTA slides) were reacted with a 0.0125 M solution of PDITC (1.6 g) in 720 ml of anhydrous DMF and 80 ml of anhydrous pyridine for 2 hours at room temperature. The solution was cannulated out, and fresh anhydrous DMF was transferred to the reactor. This wash protocol was repeated twice with DMF and twice with acetonitrile.

6. Conversion of surface terminated with an amine functionality to a surface terminated with an IC functionality Reagents: Phosgene solution 20% from Fluka (Buchs, Switerzland). ($COCl_2$; catalog # 79380). The reactor was taken out of the drying oven and quickly assembled. The boat containing 25 slides prepared as in Example was placed into the reactor and purged with $N_2$. Carefully, 800 ml of 20% phosgene solution in toluene was transferred to the reactor. The reaction was stirred at room temperature for 1 hr under nitrogen purge. The phosgene solution was then removed by cannula from the reactor and immediately quenched in a beaker containing methanol before disposing in the appropriate waste disposal. 800 ml of anhydrous acetonitrile was transferred to the reactor and stirred for 10 min. The boat containing the derivatized slides was removed from the reactor and put into a fresh anhydrous acetonitrile wash. The wash procedure with fresh anhydrous acetonitrile was repeated 2 more times. The slides were quickly dried with a stream of $N_2$ and put in a vacuum oven at 100° C. for 1 hr to remove the HCl released during the isocyanate reaction. The slides were then wrapped in aluminum foil and stored in a $N_2$ box.

7. Conversion of surface terminated with an amine functionality to a surface terminated with a succinate N-hydroxysuccinimide (SUC-NHS)

This conversion was carried out in two separate reactions: Conversion of the amine to the amidosuccinate. Reagents: Succinic anhydride (($CH_2CO)_2O$, catalog # 23,969-0), 1-methylimidazole from Aldrich (catalog # 33,609-2). Twenty five (25) prepared as described in Example 2 above (ALTA slides) were reacted with a 0.1 M solution of succinic anhydride (8.0 g) and 0.1M solution of 1-methylimidazole (6.57 g) in 800 ml of anhydrous pyridine overnight at room temperature. The slides were washed successively with 700 ml of deionized water, a 10% solution of citric acid, and 700 ml of deionized water. The slides were dried in a heated oven for a few minutes prior to the next reaction.

Conversion of the succinate to the N-hydroxysuccinimidyl ester: Reagents: N-Hydroxysuccinimide from Aldrich (NHS, catalog # 13,067-2) 1,3-Dicyclohexylcarbodiimide from Aldrich (DCC, catalog # D8,000-2). Twenty five (25) slides prepared as above (ALTA slides) were reacted with a 0.1M solution of N-hydroxysuccinimide (9.21 g) and 0.1M solution of dicyclohexyl carbodiimide (DCC) (16.51 g) in 800 ml of anhydrous tetrahydrofuran (THF) overnight at room temperature. The slides were washed successively with DMF (2×700 ml) and acetonitrile (2×700 ml).

8. Conversion of the 11-bromoundecylsilyloxy surface to a hydroxyl terminated surface (ALTO surface) (FIG. 4)

Reagents: tetraethyleneglycol (TEG) Aldrich, ($HOCH_2CH_2OCH_2CH_2)_2O$; catalog # 11,017-5]; only clean glassware dried overnight in a 120° C. heated oven was used. The reactor was removed from a drying oven and quickly assembled. The boat containing 25 silylated slides (obtained as described in Example 1) was placed into the reactor and purged with $N_2$. A 5% (w/v) solution of TEG in anhydrous DMF was prepared by addition of dry TEG (dried over molecular sieves) into 800 ml of anhydrous DMF. Using a Karl Fisher apparatus, the content of water was measured and the appropriate amount of NaH (1 equivalent (eq) per TEG eq and 1 eq per $H_2O$ eq) was carefully added in portions to the reaction mixture. The solution was heated with a heating mantel until complete dissolution of the NaH. When cooled at room temperature, the solution was transferred to the dry reactor containing 25 of 11-bromoundecyl coated slides purged with $N_2$. The reaction was run overnight at room temperature under nitrogen purge. The Teflon boat containing the slides was removed from the reactor and the slides were washed thoroughly with: 1) 2×700 ml of DMF, 2) 2×700 ml of acetonitrile, 3) 700 ml of isopropanol (2-propanol), 4) distilled water ($dH_2O$) and 5) 700 ml of acetonitrile. The slides were dried with a stream of $N_2$, wrapped in aluminum foil and stored in a dry box ($N_2$ atmosphere).

9. Conversion of the 11-bromoundecylsilyloxy surface to a 1-amino-8-hydroxyl tetraethyleneglycol surface (hydroxyl terminated surface)

Reagent: $NH_2(CH_2CH_2OCH_2CH_2)_2OH$ is prepared from TEG following the protocol described in *Bioconjugate Chem.* (1996) 7:180–186 (Frisch, et al.). The reactor was taken out of the drying oven and quickly assembled. The boat containing 11-bromoundecylsiloxy coated slides prepared as above in Example 1 was placed into the reactor and purged with $N_2$. 800 ml of 1% (w/v) solution of $NH_2$ ($CH_2CH_2OCH_2CH_2)_2OH$ in anhydrous DMF was added via a cannula. The reaction was carried out overnight at 80° C.–100° C. under nitrogen purge. The Teflon™ boat containing the slides was removed from the reactor and the slides were washed thoroughly with: 1) 2×700 ml of DMF, 2) 2×700 ml of acetonitrile, 3) 700 ml of isopropanol (2-propanol). The slides were dried with a stream of $N_2$, wrapped in aluminum foil and stored in a dry box ($N_2$ atmosphere).

10. Conversion of the terminal hydroxyls of the hydroxyl-terminated surface to amine-reactive functional groups 1) Conversion to succinimidyl carbonate (ALTO-CONHS surface): Reagents: N,N'-Disuccinimidyl carbonate from Aldrich (DCS, catalog t# 55,582-7). 4-Dimethylaminopyridine from Aldrich (DMAP, catalog # 33,245-3). Twenty five (25) slides prepared as above in Example 8 (ALTO slides) were reacted with a 0.1 M solution of N,N'-disuccinimidyl carbonate (20.5 g) and 0.1M solution of 4-dimethylaminopyridine (9.77 g ) in 800 ml of anhydrous acetonitrile overnight at room temperature. When the reaction was completed, the slides were washed thoroughly with anhydrous acetonitrile, wrapped in aluminum foil and stored in a $N_2$ box.

2) Conversion to imidazoyl carbamate (ALTO-CIM surface): Reagents: 1,1'-carbonyldiimidazole from Aldrich (CDI, catalog # 11,553-5). Twenty five (25) slides prepared as above in Example 8 (ALTO slides) were reacted with a 0.1 M solution of 1,1'-carbonyldiimidazole (12.97 g) in 800 ml of anhydrous acetonitrile overnight at room temperature. When the reaction was completed, the slides were washed thoroughly with anhydrous acetonitrile, wrapped in aluminum foil and stored in a $N_2$ box.

11. Study of amine or hydroxyl functional group density

Figure 9:
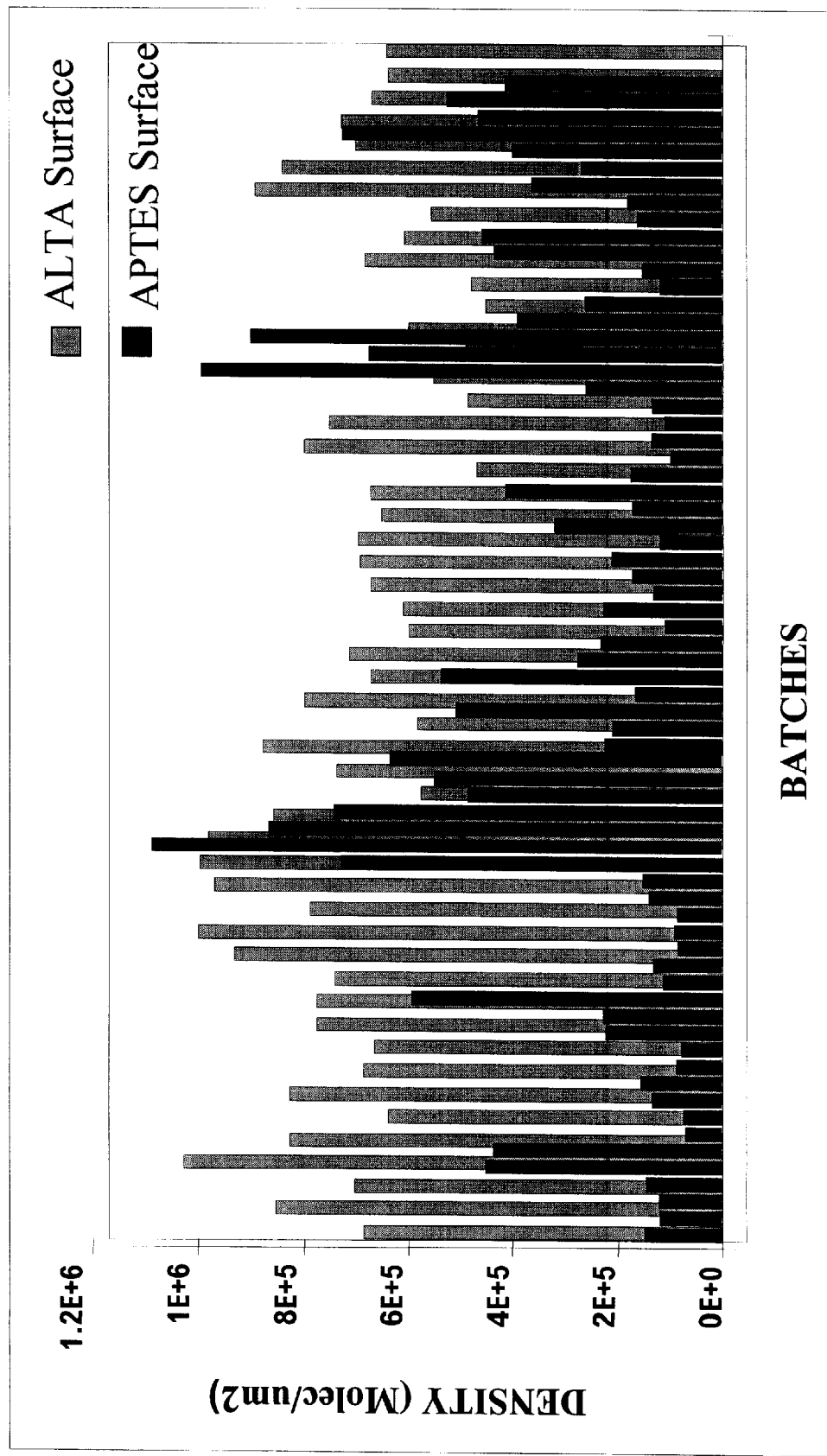
FIG. 9 is a graph depicting a density comparison of surfaces in accordance with the present invention and surfaces prepared in an alternate approach.

The amine density on amine-terminated slides was reproducibly controlled by varying the concentration of 4,7,10-Trioxa-1,13-tridecanediamine. The final amine density of the functionalized glass surface was shown to be proportional to the diamine concentration used in the reaction mixture. Five dilutions were made by dissolving the diamine reagent in acetonitrile, dimethylformamide, or dioxane at 100%, 50%, 25%, 10%, 5% (vol/vol). The reactions were carried out as described above for conversion to the amine-terminated surface. The above experiment was performed twice and based on 6 data points for each solvent at each concentration. The results are summarized in Table 1. A comparison of density for certain batches of ALTA surfaces prepared in accordance with the present invention and certain batches of APTES surfaces prepared as described herein is shown in FIG. 9.

TABLE 1

| Solvent | Dilution of Diamine | Average Amine Density (molecules per square micron) | Standard Deviation |
| --- | --- | --- | --- |
| 1,4-Dioxane | 5% | $1.55 \times 10^5$ | $3.33 \times 10^4$ |
| 1,4-Dioxane | 10% | $2.01 \times 10^5$ | $3.45 \times 10^4$ |
| 1,4-Dioxane | 25% | $3.23 \times 10^5$ | $2.42 \times 10^4$ |
| 1,4-Dioxane | 50% | $4.50 \times 10^5$ | $9.60 \times 10^4$ |
| DMF | 5% | $1.33 \times 10^5$ | $2.28 \times 10^4$ |
| DMF | 10% | $2.03 \times 10^5$ | $1.16 \times 10^4$ |
| DMF | 25% | $3.27 \times 10^5$ | $2.28 \times 10^4$ |
| DMF | 50% | — | — |
| Acetonitrile | 5% | $3.27 \times 10^4$ | $2.03 \times 10^4$ |
| Acetonitrile | 10% | $1.95 \times 10^5$ | $5.82 \times 10^4$ |
| Acetonitrile | 25% | $2.94 \times 10^5$ | $2.42 \times 10^4$ |
| Acetonitrile | 50% | $4.52 \times 10^5$ | $1.89 \times 10^4$ |
| Neet | 100% | $6.21 \times 10^5$ | $6.34 \times 10^4$ |

The hydroxyl density on the hydroxylated-terminated slides was controlled using mixtures of TEG and TEG monomethyl ether obtained from Avocado Chemical Reagents (Ward Hill, Mass.). The reactions were carried out as described above using sodium hydride to activate the hydroxyl. The surface hydroxyl density showed a linear decrease in hydroxyl density with increasing relative concentration of the TEG monomethyl ether.

12. Determination of DNA attachment by radioactive measurement of DNA probes onto amine-terminated functionalized surfaces ALTA-PDITC surfaces, ALTA-IC surfaces, ALTA-SUC-NHS and ALTA-3-BrAA surfaces were synthesized as described above. ALTO-CIM surfaces and ALTO-CONHS surfaces were synthesized as described above. Aldehydes were obtained from Cel Associate Inc., Houston, Tex. (catalog number CS-25 or CS-100. APTES-PDITC surfaces were prepared as follows: Clean glass microscope slides (25) were washed and placed in a Teflon® slide holder. Anhydrous toluene (800 ml) was placed in a 2-liter reaction vessel into which the slide holder had been placed. The toluene was stirred vigorously. To the stirring toluene was added 34.4 g (0.156 moles) of 3-aminopropyltriethoxysilane (Aldrich Chemical Company). The reaction was allowed to proceed with stirring for one hour at room temperature. The glass slides were removed from the reaction vessel and were rinsed with anhydrous toluene. The slides were then rinsed successively with acetone and 2-propanol and then were dried with a stream of nitrogen. The dry slides were placed in a vacuum oven and dried at 150° C. at 1 mm Hg for one hour. The PDITC functionality was added in a manner similar to that described above for the ALTA surfaces.

DNA was obtained by PCR amplification methods with AmpliTaq Gold® DNA polymerase (Perkin Elmer, Branchburg, N.J.) to generate cDNA's for deposition and targets for hybridization. These PCR products were isolated as single strand by Strandase enzymatic technology (Kujau, et al., *Mol. Biotechnol.* (1997) 7:333–335). Single stranded DNA targets end labeled with fluorescent dye were generated as follows: PCR amplification using a forward primer 5' end labeled with Cy3 and a reverse primer with a 5' phosphate group was used to generate a double stranded DNA. The reverse primer strand was then enzymatically digested away with Strandase® lambda exonuclease (Novegen, Madison, Wis.). Completely digested product was separated and purified away from incompletely digested product by gel electrophoresis and electroelution. In this experiment, the PCR products contained a C6-amine at the 5' end as well as the oligonucleotides (25-mer). As a control for amine specificity attachment, PCR products and oligonucleotides without amine at the 5'-end were included in this experiment. Both DNA material (PCR products and oligonucleotides) were spiked with about 5,000 cpm/$\mu$l 32P-DNA and was not accounted for in the final concentration of DNA spotted.

The PCR products (about 0.5 mg/ml) or 60 $\mu$M oligonucleotides were handspotted (0.2 $\mu$l) on functionalized slides in 0.5 M sodium carbonate (pH 10). When the spots were visibly dried, the slides were put in a humid chamber containing 0.5M sodium carbonate pH 10 overnight (about 12–24 hours). The slides were then removed from humid chamber and the spots allowed to dry at room temperature until visible dryness. The slides were washed successively with: 1) 1% ammonium hydroxide (in water), 2) fresh 1% ammonium hydroxide solution for 15 min under agitation, 3) deionized water, 4) 20×SSPE (3M NaCl, 0.02M EDTA, 0.2M sodium phosphate, pH 8) for about 20 min, 5) under running deionized water for at least 20 min. Note that for the ALTA-3-BrAA, a solution of 3% glycine in 0.5 M sodium hydroxide was used Instead of 1% ammonium hydroxide solution.

DNA was denatured as follows: the slides from above were rinsed briefly in 50 mM NaOH and then transferred to a new container of 50 mM NaOH and washed with agitation for 5 min. The slides were washed twice in deionized water with agitation for 5 min for each wash and then the slides were dried with a stream of air or nitrogen. Radioactivity measurement was carried out as follows: the spotted slides were rinsed briefly in 50 mM NaOH and then transferred to a new container of 50 mM NaOH and washed with agitation for 5 min. The slides were then washed twice in deionized water with agitation for 5 min. each wash and then were dried with a stream of air or nitrogen. The density of DNA attachment (molecules/$\mu m^2$) as determined by radioactive detection is set forth in Table 2.

TABLE 2

| Surfaces | 3'-alkyl-amine Oligo (25 mer) | No 3'-alkyl-amine Oligo (25 mer) | PCR (500 bp) 5'-alkyl-amine primer |
|---|---|---|---|
| APTES-PDITC | 10,200 | 5,100 | 1,200 |
| ALTA-PDITC | 10,800 | 5,600 | 1,300 |
| ALTA-IC | 10,900 | N/A | 2,100 |
| ALTA-SUC-NHS | 6,500 | 1,100 | 400 |
| ALTA-3-BrAA | 24,500 | <1,000 | 500–1,700 |
| ALTA-CIM | N/A | 3,200 | 470 |
| ALTA-CONHS | 6,500 | 1,900 | 550 |
| ALDEHYDES | 10,000 | 5,500 | N/A |

13. Deposition of "whole" (pre-synthesized) oligonucleotides in array format (end attachment)

1"×3" glass slides chemically derivatized with ALTA-3-BrAA surface prepared as described above in Example 4 were used as substrates to attach pre-synthesized oligonucleotides by inkjet deposition technology. Solutions of oligonucleotides (1 μM and 10 μM) in 0.05 M sodium carbonate buffer (pH 9.0) containing 0.005% Triton x-100 were inkjet-spotted onto the derivatized glass surfaces. After allowing the spots to dry to visible dryness the slides were placed in a chamber saturated with 0.05 M sodium carbonate buffer (pH 9.0) for overnight reaction. Prior to inactivation of the surface (passivation), the spots were allowed to dry again. Post-treatment (passivation) of the slides after DNA attachment was carried out as follows: The slides were placed in a Teflon™ boat, and the boat was dipped in a beaker containing 0.5 M glycine in 0.5 M sodium hydroxide at pH about 11.0 (+0 0.005% Triton X-100) for 20 minutes under stirring. The slides were then washed with copious amounts of deionized water over a period of 5 min. The wash step with clean water was repeated 2 or 3 times and the slides were dried by centrifugation.

The oligonucleotide probes (25-mers) used in this experiment were 5'-amine terminated or 5'-free and were obtained by DNA micro-synthesis using a DNA/RNA synthesizer (Model 394 form Applied BioSystems, Foster City, Calif.) and standard phosphoramidite chemistry (Beaucage, et al, Tetrahedron Letters (1981) 22:1859–1862), Matteucci, et al., J. Am. Chem. Soc. (1981) 22:1859–1862) or purchased from Operon Technologies Inc. (Alameda, Calif.). The base sequence of the probe (HCV-48-25: 5'-ACA GGG GAG TGA TCT ATG GTG GAG T-3') (SEQ ID NO:1) that was spotted onto the array corresponds to a single stranded DNA fragment contained in the genome of Hepatitis C Virus. Another sequence, a 25-mer designated Cat2, namely, 5'-ATC CGG ACG TAG GAT CAT GAG CAG G-3' (SEQ ID NO:2) was synthesized according to standard phosphoramidite chemistry and was used as a negative control for hybridization specificity.

The probes were 5'-amine terminated and labeled as Std-NH2 for oligonucleotides purchased from Operon or BSP-NH2 for oligonucleotide probes synthesized as described above. The same sequence oligonucleotides without the amine at the 5'-end were used as a control to evaluate the amine specificity of the attachment reaction of the oligonucleotide to the ALTA-3-BrAA surface prepared as described in Example 4 above.

The hybridization protocol was as follows: the arrays prepared by inkjet technology were incubated in a chamber incubation holders in 200 μl of hybridization buffer (6×SSPE, 10% SDS, 1% BSA, 10 μg/μl herring sperm DNA). The target oligonucleotide (complementary sequence of HCVB-48-25) was labeled with a cyanine dye at the 5'-end, and diluted at 100 pM in the hybridization buffer. The slides were rotated on a mechanical rotator and incubated overnight at 37 C. The holders were dismantled and the slides were washed successively with: 1) 6×SSPE+0.005% Triton X-100 (T), 2) 0.1×SSPE+T at 37 C for 15 min (with stirring), 3) ice cold 0.1×SSPE (without Triton). The slides were then centrifuged to dryness and scanned with an Avalanche Scanner from Molecular Dynamics (Sunnyvale, Calif.).

Figure 6:
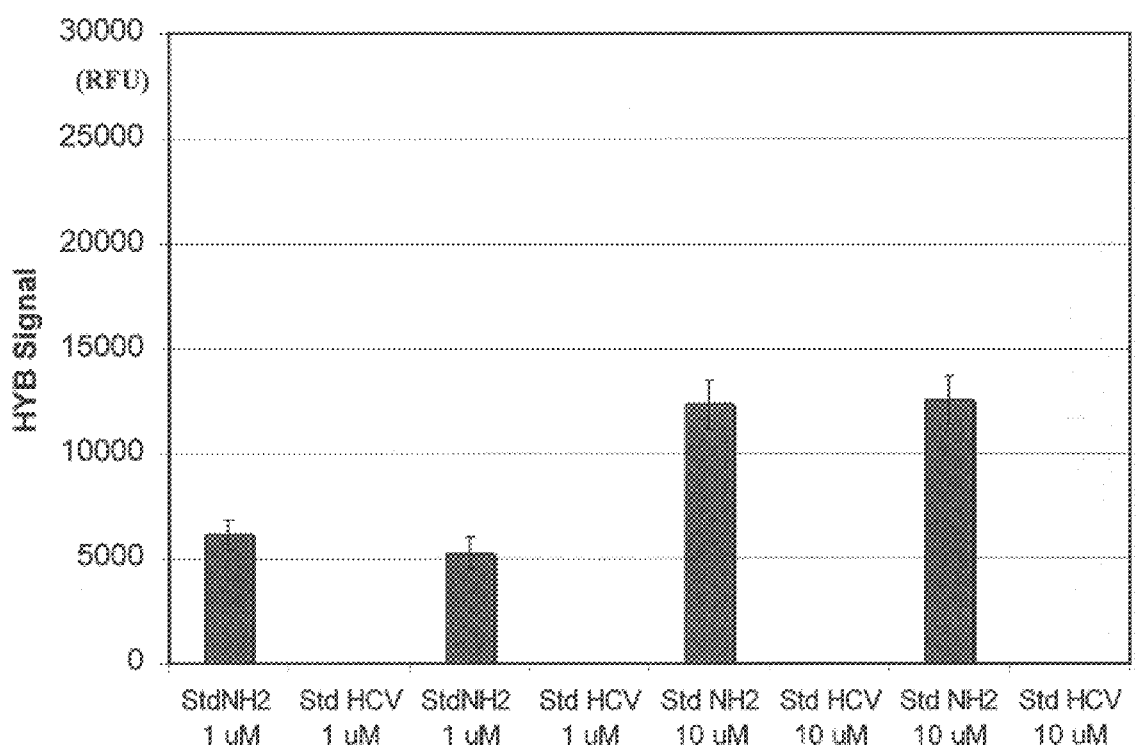
FIG. 6 is a graph depicting the results of a hybridization analysis.
Figure 7:
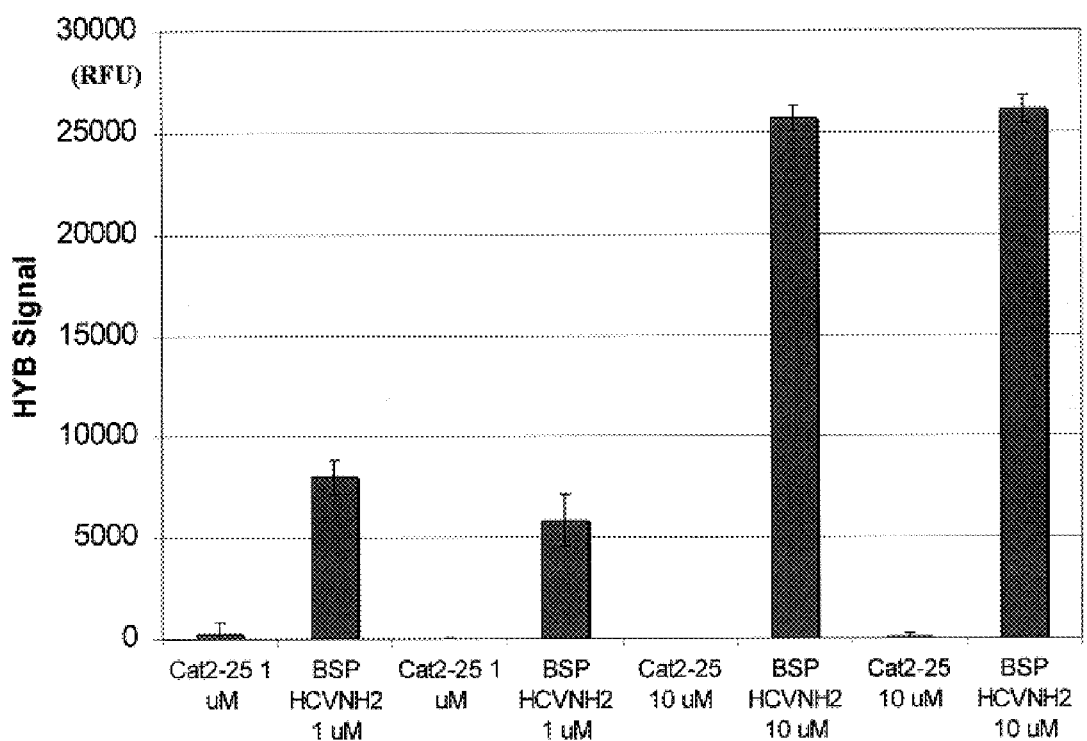
FIG. 7 is a graph depicting the results of a hybridization analysis.

The results are summarized in FIGS. 6 and 7. FIG. 6 shows a comparison of standard probes amine-terminated (StdNH2) and 5' amine-free (Std HCV) (purchased from Operon) at 1 μM and 10 μM. FIG. 7 shows a comparison of target-specific Probes amine-terminated (HCVNH2) and non-target specific Probes 3' amine-terminated (Cat2) (micro-synthesized in house) at 1 μM and 10 μM. This experiment demonstrates the very good differentiation in attachment between amine and non-amine oligonucleotide probes (25-mer), which indicates an amine-specific chemistry with the ALTA-3-BrAA surface. These results (FIG. 7) show also that the hybridization was specific since the negative controls are consistent with expected results. Finally, the experiment was preformed on eight ALTA-3-BrAA coated slides and shows a variability in hybridization signal lower than 5%, which indicates very reproducible coverage of the slides.

14. Attachment of cDNAs by UV crosslinking onto ALTA-3-BrAA Surfaces

DNA was prepared as follows: cDNA's were amplified by PCR from plasmid templates under the following conditions: 10 mM Tris pH 8.3, 3.5 mM $MgCl_2$, 25 mM KCl, 0.2 mM each dNTP, 0.4 μM each primer, 2 ng template per 100 μl reaction, 12.5 units AmpliTaq Gold DNA polymerase (Perkin Elmer) per 100 μl reaction. The cDNA amplicons were isolated using the standard ethanol precipitation procedure ("DNA Probes" George H. Keller and Mark M. Manak, Section II, p33–34, M Stockton Press, 1989). A $\frac{1}{10}^{th}$ volume 3M sodium acetate pH 6.0 plus equal volume Isopropanol were added to the DNA and the mixture was frozen until solid. The frozen was spun 10 min (14K rpm) and the supernatant was removed. The pellet was washed with 1 ml 70% ethanol, the supernatant was removed completely and the pellet was dried briefly. The pellet was resuspended in water or SSC and incubated at 65° C. for 2 hr to resuspend the pellet. The suspension was microfuged for 10 min and the supernatant was removed carefully from any particulate pellet material.

DNA solutions were made by dissolution of PCR amplicons in 1× or 3×SSC buffer at 0.25–0.5 mg/ml (estimated from agarose gel quantitation) and spotted on coated glass slides with an inkjet spotter. When DNA spots were visually dried, the glass slides were exposed to UV cross-linking at 450 mjoules in a Stratalinker Model 1800 (Stratagene, La Jolla, Calif.). The slides were then "passivated" and processed as follows: washed in 50 mM NaOH for 30 sec, dipped in a buffer (2.6 grams succinic anhydride+139.3 ml 1-methyl-2-pyrrolidinone+10.7 ml 1M sodium borate (pH 8.0) per 150 ml) for 30 min, transferred into a beaker containing boiling water for 2 min, briefly rinsed in 100% Ethanol, spun in a centrifuge to dryness. For glass slides coated with ALTA-3-BrAA surface, the protocol for passivation after spotting is as follows: the slides were soaked in 0.5M glycyne solution at pH 11.0 for 10 min (pH adjusted by 0.5M NaOH addition), washed with copious amount of deionized water, rinsed briefly in 100% ethanol, spun dry in a centrifuge.

15. Hybridization protocol for cDNA arrays with RNA target

In this experiment, gene expression levels for selected genes were measured by hybridization assay to compare gene expression levels in normal cells to chemically induced cells. RNA was isolated from ML-1 cells using the standard protocol supplied by Qiagen (Valencia, Calif.) and fluorescently labeled by enzymatic dye incorporation. Labeling protocols are described by Hacia, et al., *Nucleic Acids Research* (1998) 26(16):3865–3866. The following protocol was used for a 25 µl hybridization under a 24 mm×40 mm cover slip (Corning No. 1). The hybridization solution was mixed with the following: 22 µl of cyanine dye-tagged RNA target in 3×SSC, 1 µl poly dA40–60 (8 mg/ml) (Pharmacia 27–7988, from Amersham Pharmacia, Piscataway, N.J.), 1 µl yeast tRNA (5 mg/ml) (GibcoBRL 15401–011, from Life Technologies, Rockville, Md.), 1 µl Human CoT1 DNA (10 mg/ml) (GibcoBRL 15279-011, from Life Technologies, Rockville, Md.).

Figure 8:
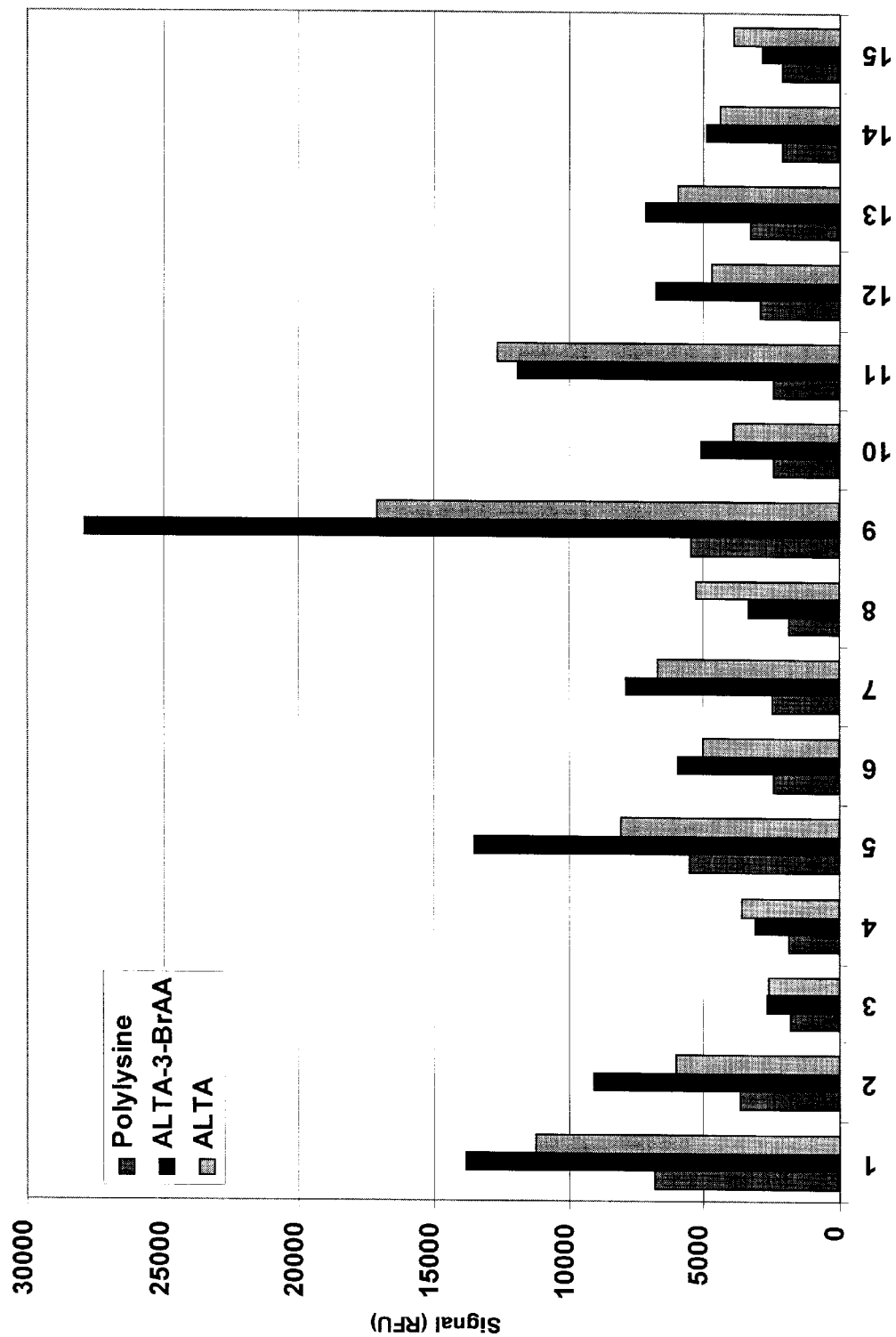
FIG. 8 is a graph depicting the results of a hybridization analysis.

The fluorescent tagged RNA target was incubated at 98° C. for 2 min in a water bath. The solution was then allowed to cool down to 45–50° C. Then, the solution was spun by a quick spin in a micro centrifuge and the pellet was collected. The tube was placed in the warm bath. 0.25 µl of 10% SDS was added, and the solution was carefully mixed with a pipette prior to being deposited onto the array. A cover slip was immediately placed onto the array, and the assembly was then placed into horizontal position into a "humidified" 50 ml Falcon tube (saturated with 3×SSC). The Falcon tube was incubated at 65 C overnight. After the hybridization, the slide was dismantled and washed with a pre-warmed buffer (0.5×SSC, 0.01% SDS) at 55° C. for 30 min. The slide was transferred in a beaker containing a liter of a second buffer (0.05×SSC) and stirred at room temperature for 10 min. The slide was then put in a centrifuge and spun for 2 min at 1000 rpm (Juan CT422, Juan Inc., Winchester Va.). The results are summarized in FIG. 8, which compares hybridization signals from 15 human genes using cDNA probes bound to three different surfaces, namely, polylysine, ALTA-3-BrAA and ALTA. As can be seen, better results were obtained by the cDNA attached to the ALTA-3-BrAA surface (higher signal) and the ALTA surface.

Example 2

Figure 10:
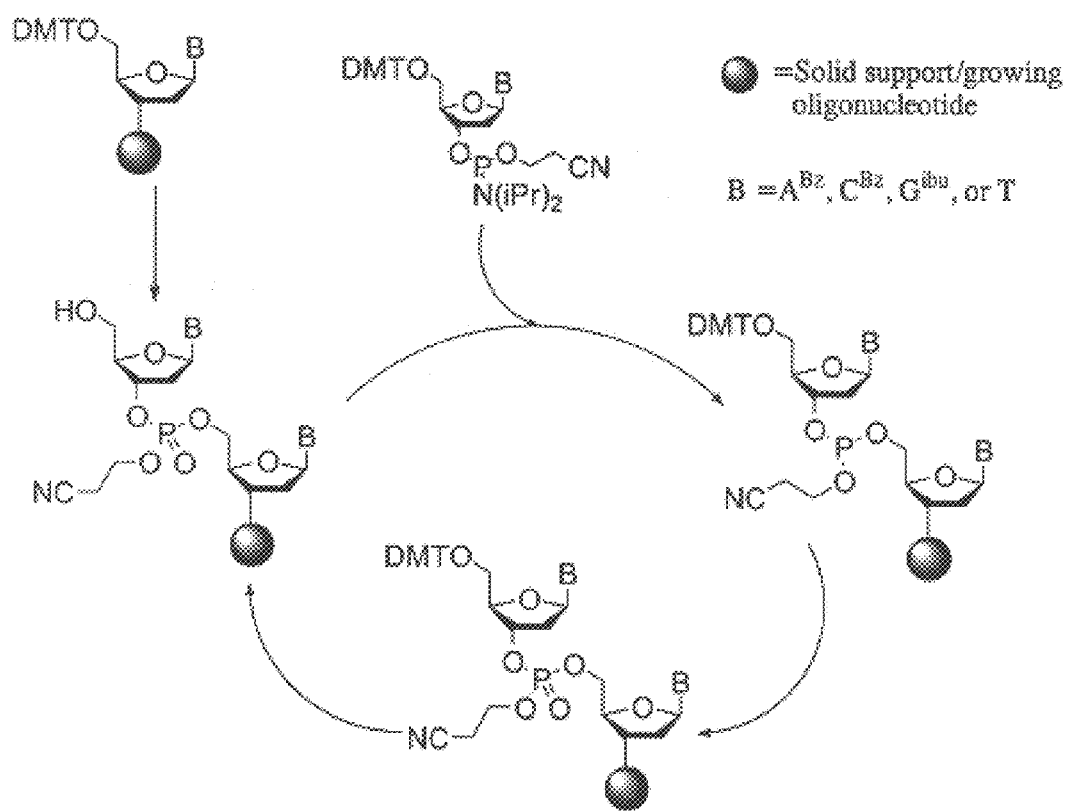
FIG. 10 is a schematic diagram depicting a synthetic method using a surface in accordance with the present invention.

The chemical synthesis of oligonucleotides was carried out on the above surfaces using known synthetic methods directed to surfaces containing a terminal primary or secondary amine. An example of such a method is the use of phosphoramidite synthons on porous glass as described by Caruthers, et al., supra. This method utilizes the reaction of acid activated nucleoside phosphoramidites with solid-phase tethered nucleoside or nucleotide hydroxyl groups. These initial nucleotides or nucleosides are attached to glass surfaces by the reaction of a succinic acid linker with an amine on the surface and also with the 3'-hydroxyl of the desired nucleoside or nucleotide. The oligonucleotide chain is elongated by the addition of the reactive phosphoramidite intermediate to the surface. Under these reaction conditions, a phosphite triester internucleotide bond is formed to extend a growing oligonucleotide chain. The resulting solid-phase mixture is exposed to a capping agent designed to cap off failure sequences and cleave addition products to the heterocyclic bases. The nascent phosphite internucleotide linkage is oxidized to the corresponding phosphotriester derivative, using a mild oxidizing agent, before the next hydroxyl group is exposed by deprotection of the 4,4'-dimethoxytrityl (DMT) using a large excess of a weak acid in an organic solvent. This cycle is repeated until the oligonucleotide of desired length and sequence is obtained. The above is summarized in the scheme depicted in FIG. 10.

Oligonucleotides were synthesized using the above methods on planar ALTA slide surfaces prepared as described in Example 1, part 2, above. Phosphoramidite DNA synthesis was carried out by flooding the surface sequentially with the various reagents described above. The reagents for these experiments were obtained from Glen Research, Sterling Va. The final oligonucleotide products were cleaved from the surface and analyzed using anion-exchange HPLC and MALDI/TOF Mass Spectroscopy. The oligonucleotides synthesized on these ALTA surfaces were shown to be identical to authentic samples. Four oligonucleotide homopolymers of thymidine of different length were synthesized on a single planar ALTA surface by jetting the reagents onto defined coordinates. These sequences were of length 7, 10, 15, and 20 nucleotides in length. The products were cleaved from the surface and separated by ionexchange chromatography. The oligonucleotides synthesized in this experiment were analyzed by MALDI/TOF mass spectroscopy and were found to be identical to authentic samples.

In an analogous fashion, oligonucleotides were synthesized on ALTO slide surfaces prepared as described above in Example 1, part 8. These ALTO surfaces contained terminal hydroxyl functional groups, which were reacted directly with phosphoramidite reactive intermediates to produce oligonucleotides linked to the surface through a phosphodiester bond. These surfaces produce an attachment linkage that is stable to most conditions that does not degrade the glass itself. These experiments produced planar glass substrates with covalently attached oligonucleotides. These substrates were used to demonstrate hybridization of radio-labelled complementary oligonucleotides. An oligonucleotide of a predetermined sequence of 25 nucleotides was synthesized by flooding the planar surface with reagents in a sequential fashion. This surface was then sectored using a silicon rubber gasket and various concentrations of radiolabelled oligonucleotide were exposed to the surface at room temperature for 22 hr under the hybridization conditions described above. The resulting radioactive hybridizations were quantified using a Phosphorimager from Molecular Dynamics, Sunnyvale Calif.

Oligonucleotides were also synthesized on these surfaces by the methods described by Dellinger, et. al. *Solid-Phase Synthesis of Oligodeoxyribonucleotides Using Phosphoramidite Synthons in a Two Step Synthesis Cycle*, (XII International Round Table Nucleosides, Nucleotides, and their Biological Applications, Montpellier, France, September 1998). ALTA slide surfaces were converted to an acid cleavable linker system described by Rampal, et al. *Novel Ligands Useful in Post-Synthesis Processing of Oligonucleotides* (Federation of American Societies for Experimental Biology, Washington, D.C., 1986).

Synthesis of 5'-Acid Cleavable Linker

Figure 11:
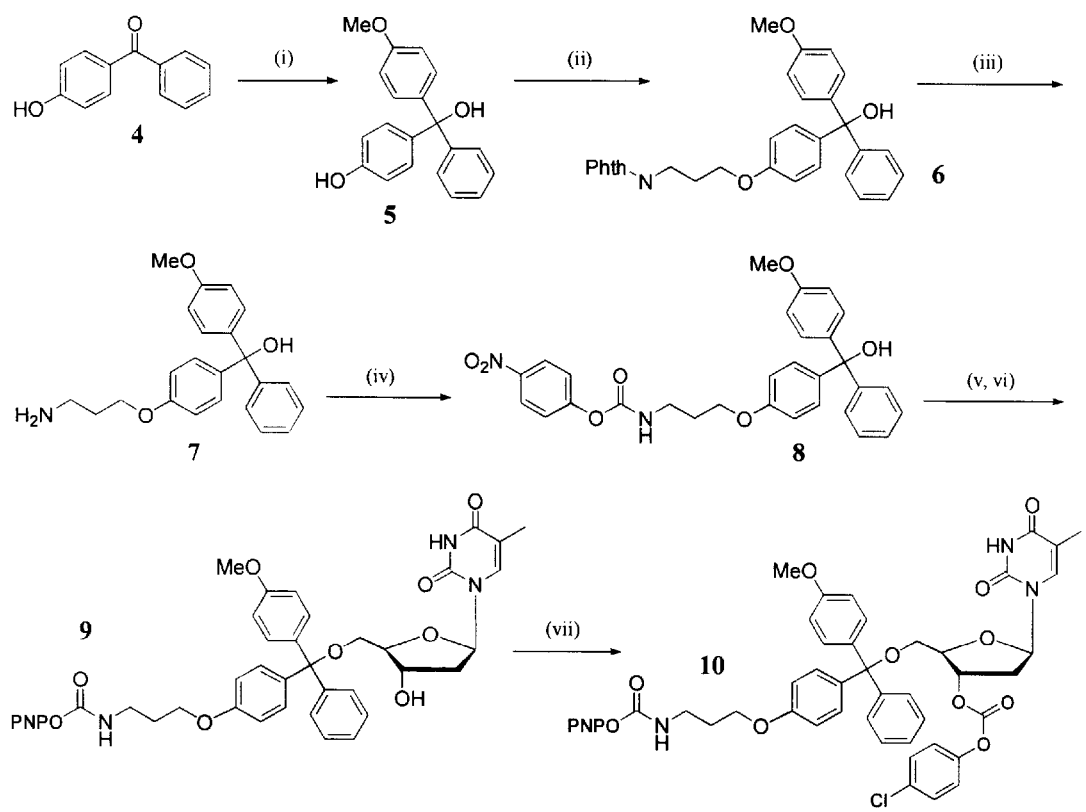
FIG. 11 is a schematic diagram depicting a synthetic method using a surface in accordance with the present invention having a bifunctional linker.

The linker was synthesized by the method summarized in the scheme set forth in FIG. 11. Grignard attack on 4-hydroxybenzophenone 4 with 3 equivalents of 4-anisyl magnesium bromide in THF, obtained from ALFA Chemical Co. (Ward Hill, Mass.), yielded trityldiol 5 in good yield. Williamson ether condensation with 3-bromopropyl phthalimide, followed by deprotection in refluxing ethanolic hydrazine hydrate, yielded amine 7 in excellent yield. The activated carbamate moiety in 8 was then installed by treatment of 7 with bis-4-nitrophenyl carbonate. The trityl alcohol of 8 was activated to the trityl chloride in refluxing acetyl chloride/hexanes prior to coupling with 2'-deoxythymidine in pyridine to yield 9. Finally, 3'-protection with 4-chlorophenyl chloroformate in pyridine proceeded analogously to that during the phosphoramidite synthesis yielding linker 10 in excellent yield. The yield over seven steps was 32%.

4-Hydroxy, 4'-methoxytrityl alcohol 5

To 4-hydroxybenzophenone (12.5 g, 63.1 mmol) in THF (250 mL) under ice cooling was added dropwise 4-anisyl magnesium bromide (350 mL of a 0.5 M solution in THF, 175 mmol) over 1 h. Cooling was removed and the mixture stirred at ambient temperature and under inert atmosphere for 16 h. Most of the THF was removed in vacuo and the residue partitioned between water and ether. The ether layer was extracted with sat. NaHCO$_3$ and brine, dried (MgSO$_4$), and evaporated to yield a red oil. The oil was purified by silica gel chromatography (sgc) using a gradient of 0–4% ethanol in dichloromethane/triethylamine 99.5/0.5. The title compound was isolated as a pale yellow oil (14.2 g, 73.5%); R$_f$ 0.14; $^1$H NMR (CDCl$_3$) 3.78 (3H, s), 6.75 (2H, d, J=8.8), 6.83 (2H, d, J=8.8), 7.11 (2H, d, J=8.8), 7.17 (2H, d, J=8.8), 7,25–7.32 (5H, m); $^{13}$C NMR (CDCl$_3$); MS (ESI-) m/z 305 (M- 1, 100); (ESI+) m/z 635 (M$_2$+Na, 33), 289 (M—H$_2$O, 100);

4-(3-Phthalimidopropoxy), 4'-methoxytrityl alcohol 6

To alcohol 5 (10.0 g, 32.6 mmol) in toluene (250 mL) was added anhydrous potassium carbonate (12.3 g, 65.2 mmol), 3-bromopropyl phthalimide (35.7 g, 97.8 mmol), and a single dry potassium iodide crystal. The mixture was refluxed for 24 hours, cooled, and solvent removed in vacuo. The residue was partitioned between dichloromethane and water, and the dichloromethane layer extracted with sat. NaHCO$_3$ and brine, dried (MgSO$_4$), and evaporated to yield a pale yellow oil. The oil was purified by sgc using a gradient of 0–2% ethanol in dichloromethanel triethylarnine 99.8/0.2. The title compound was isolated as a pale yellow oil (15.5 g, 70.7%); R$_f$ 0.41; $^1$H NMR (CDCl$_3$) 2.14–2.18 (2H, m), 2.91 (1H, s), 3.78 (3H, s), 3.87 (2H, t, J=7.0), 3.99 (2H, t, J=6.2), 6.71 (2H, d, J=8.8), 6.80 (2H, d, J=8.8), 7.10 (2H, d, J=8.8), 7.15 (2H, d, J=8.8), 7.23–7.28 (5H, m), 7.66–7.69 (2H, m), 7.79–7.81 (2H, m); $^{13}$C NMR 28.3, 35.4, 55.2, 65.6, 37.8, 113.0, 113.6, 123.2, 126.9, 127.7, 129.0, 129.1, 132.0, 133.9, 139.4, 139.5, 147.3, 157.7, 158.5, 168.3; MS (FAB+) m/z 493 (M, 25), 476 (M—OH, 100);

4-(3-Aminopropoxy), 4'-methoxytrityl alcohol 7

Alcohol 6 (12.5 g, 25.3 mmol) was dissolved in ethanol (310 mL), and hydrazine hydrate (12.7 mL, 0.249 mol) added. The mixture was refluxed over 1 hr, cooled, and the copious precipitate removed by filtration. Ethanol was removed in vacuo and the residue partitioned between water and ether. 1 M HCl was added dropwise to the mixture to pH 3, at which point the ether layer was discarded. More ether was added and the pH taken to pH 12 with 1 M NaOH. The ether layer was collected, dried (MgSO$_4$), and solvent removed to furnish the title compound as a clear, colorless oil (8.30 g, 90.3%); $^1$H NMR (CDCl$_3$) 1.79–1.86 (2H, m), 2.20 (1H, br s), 2.77 (2H, t, J=7.0), 3.75 (3H, s), 3.95 (2H, t, J=6.2), 6.77–6.80 (4H, m), 7.14–7.18 (4H, m), 7.20–7.27 (5H, m); $^{13}$C NMR (CDCl$_3$) 32.6, 39.0, 55.1, 57.8, 65.7, 81.0, 112.9, 113.4, 126.8, 127.6, 127.7, 129.1, 139.7, 147.5, 157.7, 158.3; MS (ESI-) m/z 362 (M-1, 100); (ESI+) m/z 364 (M+1, 100), 727 (M$_2$+1, 37);

4-(3-(4-Nitrophenoxycarboxy)-amino), 4'-methoxytrityl alcohol 8

Amino alcohol 7 (5.40 g, 14.8 mmol) was dissolved in dichloromethane (320 mL) and bis-4-nitrophenyl carbonate (4.50 g, 14.8 mmol) added. The mixture was stirred for 24 h, extracted exhaustively with NaHCO$_3$ (sat.), washed with brine, dried (MgSO$_4$), and solvent evaporated to yield an orange oil. The oil was purified by sgc using a gradient of 0–3% ethanol in dichloromethane and the title compound isolated as a pale yellow oil (6.90 g, 88.2%); $^1$H NMR (CDCl$_3$) 2.02–2.08 (2H, m), 3.05 (1H, br s), 3.45–3.53 (2H, m), 3.77 (3H, s), 4.05 (2H, t, J=5.6), 5.70 (1H, t, J=5.6), 6.79–6.82 (4H, m), 7.13–7.17 (4H, m), 7.23–7.30 (7H, m), 8.18 (2H, d, J=9.1); $^{13}$C NMR (CDCl$_3$) 28.8, 39.1, 55.1, 65.8, 81.3, 113.1, 113.6, 121.9, 125.0, 127.0, 127.7, 127.8, 129.1, 129.2, 139.3, 139.9, 144.6, 147.2, 153.1, 155.8, 157.5, 158.6; MS (FAB+) m/z 528 (M, 28), 511 (M—OH, 100);

5'-(4-(3-(4-Nitrophenoxycarbonyl)-amino), 4'-methoxytrityl)-2'-deoxythymidine 9

To trityl alcohol 8 (6.60 g, 12.5 mmol) was added hexanes (240 mL) and acetyl chloride (40 mL). The mixture was refluxed over 16 hr, cooled to −20° C., and the supernatant decanted. The remaining red oil was foamed under vacuum, and dissolved in pyridine (100 mL). 2'-Deoxythymidine (2.73 g, 11.3 mmol) was added and the mixture stirred over 2 hr. Pyridine was removed in vacuo and the oil partitioned between dichloromethane and 5% sodium carbonate solution. The organic layer was washed with brine, dried, and purified by sgc with 0–5% ethanol/dichloromethane as eluent. The title compound was isolated as a pale yellow glassy solid (8.19 g, 87.1%); $^1$H NMR (CDCl$_3$) 1.47 (3H, s), 2.05–2.16 (2H, m), 2.26–2.55 (2H, m), 3.35–3.53 (5H, m), 3.78 (3H, s), 4.02–4.10 (3H, m), 4.58 (1H, br s), 5.88 (1H, t, J=5.9), 6.40 (1H, t, J=7.0), 6.80–6.85 (4H, m), 7.21–7.27 (9H, m), 7.40 (2H, d, J=7.4), 7.59 (1H, s), 8.22 (2H, d, J=8.9), 9.90 (1H, s); $^{13}$C NMR (CDCl$_3$); 11.7, 28.9, 38.9, 40.8, 53.4, 55.2, 63.6, 65.8, 72.2, 84.8, 86.3, 86.8, 111.1, 113.2, 113.7, 121.9, 124.9, 127.1, 127.9, 128.0, 129.9, 130.0, 135.1, 135.9, 144.2, 144.6, 150.6, 153.2, 155.9, 157.6, 158.6, 164.1; MS (FAB+) m/z 753 (M+1, 100);

5'-(4-(3-(4-Nitrophenoxycarbonyl)-amino), 4'-methoxytrityl)-3'-(4-chlorophenoxycarbonyl)-2'-deoxythymidine 10

To nucleoside 9 (2.35 g, 3.12 mmol) in pyridine (35 mL) was added 4-chlorophenyl chloroformate (478 μL, 3.75 mmol). The mixture was stirred for 2 h at which point the solvent was removed under reduced pressure. The residue was dissolved in dichloromethane, washed with 5% sodium carbonate and brine, dried (MgSO$_4$), and solvent removed in vacuo to yield a pale yellow oil. The title compound was isolated by sgc using 0–3% ethanol/dichloromethane as eluent as a pale yellow glassy solid (2.55 g, 90.0%); $^1$H NMR (CDCl$_3$) 1.43 (3H, s), 2.05–2.08 (2H, m), 2.48–2.78 (2H, m), 3.43–3.60 (4H, m), 3.78 (3H, s), 4.02–4.10 (2H, m), 4.32 (1H, m), 5.40–5.46 (1H, m), 6.00–6.06 (1H, m), 6.50–6.56 (1H, m), 6.80–6.85 (4H, m), 7.11 (2H, d, J=8.8), 7.21–7.27 (9H, m), 7.60–7.73 (2H, m), 7.59 (1H, s), 8.20 (2H, d, J=8.8), 8.61 (2H, m), 10.06 (1H, br s); $^{13}$C NMR (CDCl$_3$); 11.5, 28.9, 37.9, 38.8, 55.1, 63.6, 65.7, 79.7, 83.5, 84.3, 87.1, 111.5, 113.2, 113.7, 121.8, 122.1, 123.6, 124.9, 127.2, 127.9, 128.0, 129.5, 129.9, 129.9, 130.0, 131.6, 135.1, 135.9, 143.9, 144.5, 149.1, 149.5, 150.5,152.6, 153.1, 155.9, 157.7, 158.7, 163.9;

Derivatization of ALTA Glass Surfaces with 5'-Acid Cleavable Linker

Planar glass slides containing the ALTA surface (prepared as described above in Example 1, part 2) were exposed to a 0.1 M solution of 10 in dioxane/pyridine (9/1) overnight. Washing with dioxane, methanol, and ether was followed by capping overnight of any unreacted amine sites with 0.1 M 4-nitrophenyl acetate in the same solvent mixture. In a final capping step, the surface was treated with chlorotrimethylsilane in pyridine. Quantitation of nucleoside loading was achieved by acid cleavage of the 3'-Arco-2'-deoxythymidine from the surface followed by UV analysis at 280 nm.

DNA Synthesis using Two-Step Peroxy-Acid Synthesis Cycle

Figure 12:
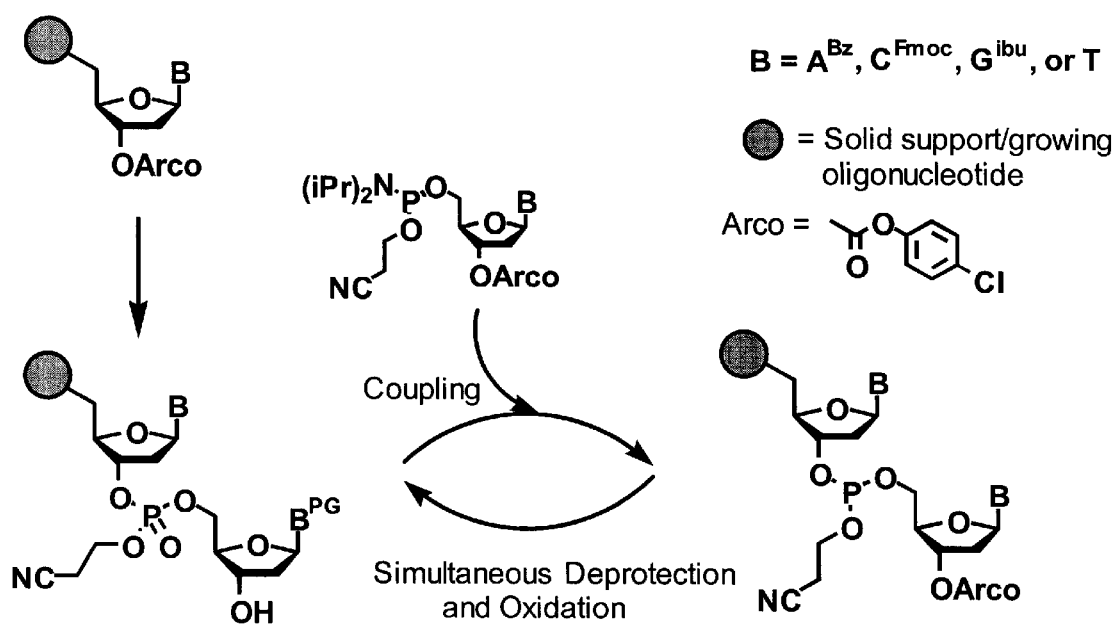
FIG. 12 is a schematic diagram depicting a synthetic method using a surface in accordance with the present invention.

Oligonucleotides were synthesized using a two-step synthesis cycle on these ALTA surfaces that consisted of flooding an oxidative deprotection reagent followed by coupling with an 3'-Aryloxycarbonyl (Arco) protected 5'-nucleoside phosphoramidite by the scheme depicted in FIG. 12. 3'-Arco modified nucleoside phosphoramidites were dissolved in anhydrous acetonitrile to a concentration of 0.1 M. The oxidative deprotection mixture was prepared fresh by mixing two previous prepared solutions, namely, Solution A and Solution B. Solution A: 3.0 % w/v lithium hydroxide monohydrate (10 mL), 1.5 M 2-amino-2-methyl-1-propanol pH 10.3 (15 mL), 1,4-dioxane (17.5 mL). Solution B: 1,4-Dioxane (32.5 mL), 50–83% 3-chloroperbenzoic acid (1.78 g), 30% hydrogen peroxide (12 mL). The initial pH of the deprotection mixture was 9.60±0.05. The Arco protecting group was removed with five 15 sec treatments with the Arco deprotection mixture, alternated with five 15 sec wait periods. After deprotection the surface was washed extensively with 1,4-dioxane then acetonitrile to ensure anhydrous conditions for the next coupling. Each synthesis cycle took approximately 7 minutes to complete. After the addition of the final nucleotide, the terminal 3'-Arco protecting group was removed, the ALTA dried, and treated with 40% methyl amine in water at 55° C. for 15 min to remove the heterocyclic base protecting groups. The resulting oligodeoxynucleotide was removed from the surface by treatment with 80% acetic acid for 30 min at room temperature. The acetic acid was removed under vacuum and the oligonucleotide characterized by ion exchange HPLC and MALDI/TOF mass spectroscopy.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for immobilizing a substance to a surface, said method comprising:
   (a) combining (i) a surface comprising a linking group consisting of a first portion comprising a hydrocarbon chain, optionally substituted, and a second portion comprising an alkylene oxide or an alkylene imine wherein said alkylene is optionally substituted and wherein one end of said first portion is attached to the surface and one end of said second portion is attached to the other end of said first portion by means of an amine or an oxy functionality and wherein said second portion terminates in an amine or a hydroxy functionality and (ii) the substance to be immobilized, and
   (b) treating said combination under conditions wherein said substance becomes attached to said surface through the intermediacy of said linking group.

2. A method according to claim 1 wherein said hydrocarbon chain is 6 to 20 carbon atoms in length.

3. A method according to claim 1 wherein said alkylene oxide is a polyoxyalkylene chain represented by the formula:

wherein m, n and p, are each independently an integer of 1 to 4, and q is an integer of 1 to 24.

4. A method according to claim 3 wherein m, n and p are 2, and q is 2 or 4 and wherein said hydrocarbon chain is an alkyl chain of 8 to 12 carbon atoms in length.

5. A method according to claim 1 wherein said alkyl chain is attached to said surface by means of a silyloxy linkage.

6. A method according to claim 1 wherein said substance is a ligand or a receptor.

7. A method according to claim 1 wherein said substance is a nucleoside, a nucleotide or a polynucleotide.

8. A method according to claim 1 wherein said substance comprises an amine-specific reactive functional group and said alkylene chain or said alkylene imine terminates in an amine group.

9. A method according to claim 1 wherein said substance comprises an alcohol-specific reactive functional group and said alkylene chain or said alkylene imine terminates in a hydroxy group.

10. A method according to claim 1 wherein said alkylene imine is a polyiminoalkylene chain represented by the formula:

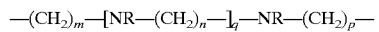

wherein R is H or alkyl, m, n and p, are each independently an integer of 1 to 4, and q is an integer of 1 to 24.

11. A composition comprising a surface having attached thereto, at a density of 1 to about $1 \times 10^7$ per square micron, a compound of the formula:

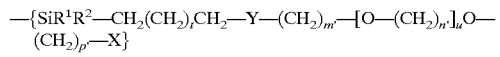

wherein:
   $R^1$ and $R^2$ are independently O, alkyl, aryl, alkoxy, aryloxy or halogen,
   t is an integer of 2 to 24,
   m', n', and p' are each independently integers of 2 to 3,
   u is an integer of 1 to 6,
   Y is O or $NR^3$ wherein $R^3$ is H or alkyl and
   X is OH, $NR^4R^5$ wherein $R^4$ and $R^5$ are each independently H or alkyl or L—D wherein L is a linking group or a bond and D is a ligand or a receptor.

12. A composition according to claim 11 wherein D is a nucleotide, nucleoside or a polynucleotide.

13. A composition according to claim 11 wherein t is 9, u is 2, n' is 2, m' and p' are 3, Y is NH and X is $NH_2$.

14. A composition according to claim 11 wherein t is 9, u is 2, m', n' and p' are 2, Y is NH and X is OH.

15. A composition according to claim 11 wherein t is 9, u is 2, m', n', and p' are 2, Y is O and X is OH.

16. A composition according to claim 11 wherein said density is about $10^3$ to about $2 \times 10^6$ per micron square.

17. A composition according to claim 11 wherein L comprises a labile functionality.

18. A combination of compositions comprising:
   (a) a composition comprising a surface having attached thereto, at a density of 1 to about $1 \times 10^7$ per square micron, a compound of the formula:

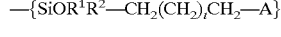

wherein:
R[1] and R[2] are independently O, alkyl, alkyl, aryl, alkoxy, aryloxy, or halogen,
t is an integer of 2 to 24, and
A is a leaving group, and
(b) a composition of the formula:

wherein:
m', n', p' and s' are each independently integers of 2 to 3,
u is an integer of 1 to 6,
W is OH or NHR[6] wherein R[6] is H or alkyl and
X is OH, NR[4]R[5] wherein R[4] and R[5] are each independently H or alkyl or L'—D' wherein L' is a linking group or a bond and D' is a ligand or a receptor.

19. A combination of compositions according to claim 18 wherein t is 9, u is 2, n' is 2, m' and p' are 3, W is $NH_2$, A is bromo, and X is $NH_2$.

20. A combination of compositions according to claim 18 wherein t is 9, u is 2, m', n' and p' are 2, W is $NH_2$, A is bromo, and X is OH.

21. A combination of compositions according to claim 18 wherein t is 9, u is 2, m', n', and p' are 2, W is OH, A is bromo, and X is OH.

22. A combination of compositions according to claim 18 wherein said density is $10^3$ to $2\times10^6$ per micron square.

23. A combination of compositions according to claim 18 wherein D is a nucleotide, nucleoside or a polynucleotide.

24. A method for immobilizing a substance to a surface, said method comprising:
(a) combining in a reaction medium
(i) said substance,
(ii) a first composition comprising a surface having attached thereto, at a density of 1 to about $1\times10^7$ per square micron, a compound of the formula:

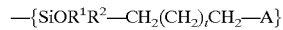

wherein:
R[1] and R[2] are independently O, alkyl, alkyl, alkyl, aryl, alkoxy, aryloxy or halogen,
t is an integer of 2 to 24, and
A is a leaving group, and
(iii) a second composition of the formula:

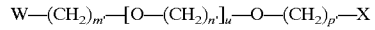

wherein:
m', n', p' and s' are each independently integers of 2 to 3,
u is an integer of 1 to 6,
W is OH or NHR[6] wherein R[6] is H or alkyl and
X is OH, NR[4]R[5] wherein R[4] and R[5] are each independently H or alkyl or —L—D' wherein L is a linking group or a bond and D' is an amine or a hydroxy group and
(b) treating said medium under conditions sufficient to permit said second composition to attach to said first composition and said substance to attach to said second composition.

25. A method according to claim 24 wherein t is 9, u is 2, n' is 2, m' and p' are 2, W is $NH_2$, A is bromo, and X is $NH_2$.

26. A method according to claim 24 wherein t is 9, u is 2, m', n' and p' are 2, W is $NH_2$, A is bromo, and X is OH.

27. A method according to claim 24 wherein t is 9, u is 2, m', n', and p' are 2, W is OH, A is bromo, and X is OH.

28. A method according to claim 24 wherein said density is about $10^3$ to about $2\times10^6$ per micron square.

* * * * *